United States Patent
Lazzari et al.

(10) Patent No.: US 6,441,166 B1
(45) Date of Patent: Aug. 27, 2002

(54) STERICALLY HINDERED AMINE COMPOUNDS

(75) Inventors: Dario Lazzari, Casalecchio di Reno; Graziano Zagnoni, Vergato, both of (IT); Stephen Mark Andrews, New Fairfield, CT (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/459,697

(22) Filed: Dec. 13, 1999

Related U.S. Application Data

(60) Provisional application No. 60/112,164, filed on Dec. 14, 1998.

(51) Int. Cl.$^7$ ............... C07D 251/42; C07D 251/48; C07D 251/54; C07D 295/02; A61K 31/53
(52) U.S. Cl. ............ 544/209; 544/212; 546/256
(58) Field of Search ............... 544/209, 212; 546/256

(56) References Cited

U.S. PATENT DOCUMENTS

| | | | |
|---|---|---|---|
| 4,238,613 A | 12/1980 | Rasberger et al. | 546/190 |
| 4,293,468 A | 10/1981 | Rody | 260/45.8 |
| 4,369,275 A | 1/1983 | Rody | 542/427 |
| 4,419,472 A | 12/1983 | Berner et al. | 524/102 |
| 4,532,279 A | 7/1985 | Karrer | 524/102 |
| 4,670,488 A | 6/1987 | Maegawa et al. | 524/103 |
| 4,948,889 A | 8/1990 | Cantatore et al. | 544/198 |

FOREIGN PATENT DOCUMENTS

| | | |
|---|---|---|
| EP | 0107805 | 5/1984 |
| EP | 0209126 | 1/1987 |
| EP | 0782994 | 7/1997 |
| EP | 0849327 | 6/1998 |
| EP | 0850938 | 7/1998 |
| GB | 2276878 | 10/1994 |

Primary Examiner—Richard L. Raymond
Assistant Examiner—Venkataraman Balasubramanian
(74) Attorney, Agent, or Firm—Luther A. R. Hall; David R. Crichton

(57) ABSTRACT

A product containing 5 to 85% of a group (A-1-a) and/or (A-1-b)

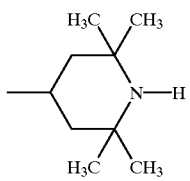

(A-1-a)

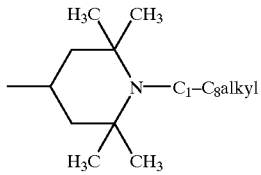

(A-1-b)

and 15 to 95% of a group (A-2),

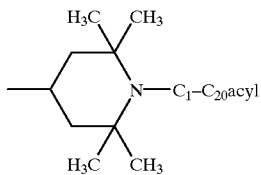
(A-2)

the total sum of the groups (A-1-a), (A-1-b) and (A-2) being 100%, is useful for stabilizing an organic material against degradation induced by light, heat or oxidation.

11 Claims, No Drawings

STERICALLY HINDERED AMINE COMPOUNDS

This application claims the benefit under 35 U.S.C. 119(e) of U.S. Provisional Application No. 60/112,164, filed Dec. 14, 1998.

The present invention relates to products containing 1-($C_1$–$C_{20}$acyl)-2,2,6,6-tetramethyl-4-piperidyl groups as well as 2,2,6,6-tetramethyl-4-piperidyl groups the latter of which may optionally be substituted on the piperidyl nitrogen by $C_1$–$C_8$alkyl, to the use of these products as light stabilizers, heat stabilizers and oxidation stabilizers for organic materials, particularly synthetic polymers, and to the organic materials thus stabilized. 2,2,6,6-tetramethylpiperidine derivatives are, for example, disclosed in EP-A-209,126, EP-A-849,327, DE-A-2,718,458 (U.S. Pat. No. 4,293,468 and U.S. Pat. No. 4,369,275), DE-A-2,755,340 (U.S. Pat. No. 4,238,613), EP-A-52,579 (U.S. Pat. No. 4,419,472), EP-A-107,805, DE-A-3,403,116 (U.S. Pat. No. 4,532,279), U.S. Pat. No. 4,670,488 and U.S. Pat. No. 4,948,889. In detail, the present invention relates to a product containing 5 to 85%, for example 15 to 85%, 15 to 80%, 15 to 75% or 5 to 75%, 15 to 70% or 20 to 70%, 15 to 60%, 20 to 60%, 30 to 60%, 25 to 50%, 40 to 60% or 50% of a group (A-1-a) and/or (A-1-b)

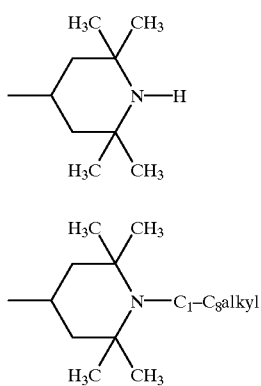

and 15 to 95%, for example 15 to 85%, 20 to 85%, 25 to 85% or 25 to 95%, 30 to 85% or 30 to 80%, 40 to 85%, 40 to 80%, 40 to 70% or 50 to 75%, 40 to 60% or 50% of a group (A-2),

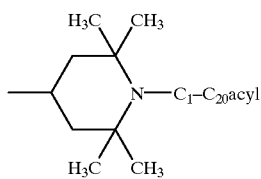

the total sum of the groups (A-1-a), (A-1-b) and (A-2) being 100%.

A product which corresponds to the formula (I) as defined under a), the formula (II) as defined under b), the formula (V) as defined under c), the formula (VI) as defined under d), the formula (VII) as defined under e), a reaction product as defined under f), or which corresponds to the formula (IX) as defined under g), the formula (X) as defined under h), the formula (XI) as defined under i), the formula (XII) as defined under j), the formula (XIII) as defined under k), the formula (XIV) as defined under l), the formula (XVI) as defined under m), the formula (XVII) as defined under n), the formula (XVIII) as defined under o) or the formula (XIX) as defined under p) is preferred.

a) a product mixture of the formula

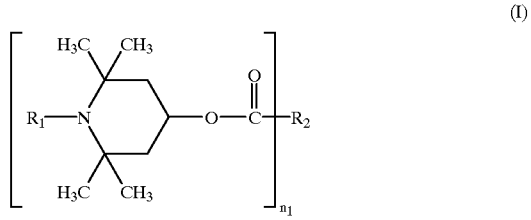

in which the radicals $R_1$ independently of one another are hydrogen, $C_1$–$C_8$alkyl or $C_1$–$C_{20}$acyl with 5 to 85% of the total sum of the radicals $R_1$ independently of one another being hydrogen or $C_1$–$C_8$alkyl and the remaining radicals $R_1$ being $C_1$–$C_{20}$acyl;

$n_1$ is 2 or 4, if $n_1$ is 2, $R_2$ is $C_1$–$C_{14}$alkylene or bis{($C_1$–$C_{20}$alkyl)oxycarbonyl}$C_4$–$C_{10}$alkanetetrayl, if $n_1$ is 4, $R_2$ is $C_4$–$C_{10}$alkanetetrayl;

b) a product mixture of the formula

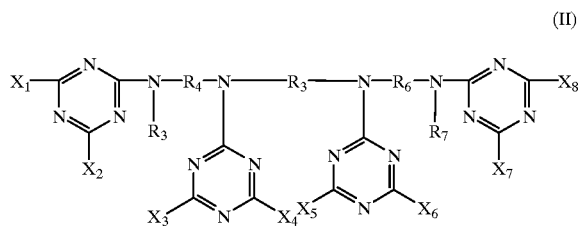

in which $R_3$ and $R_7$ independently of one another are hydrogen or $C_1$–$C_{12}$alkyl, $R_4$, $R_5$ and $R_6$ independently of one another are $C_2$–$C_{10}$alkylene, and $X_1$, $X_2$, $X_3$, $X_4$, $X_5$, $X_6$, $X_7$ and $X_8$ independently of one another are a group of the formula (III),

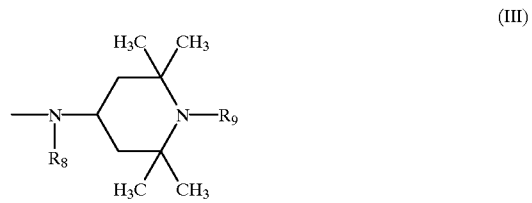

in which $R_8$ is hydrogen, $C_1$–$C_{12}$alkyl, $C_5$–$C_{12}$cycloalkyl, $C_1$–$C_4$alkyl-substituted $C_5$–$C_{12}$cycloalkyl, phenyl, —OH— and/or $C_1$–$C_{10}$alkyl-substituted phenyl, $C_7$–$C_9$phenylalkyl, $C_7$–$C_9$phenylalkyl which is substituted on the phenyl radical by —OH and/or $C_1$–$C_{10}$alkyl; or a group of the formula (IV),

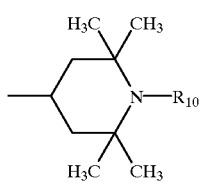
(IV)

and the radicals $R_9$ and $R_{10}$ independently of one another are hydrogen, $C_1-C_8$alkyl or $C_1-C_{20}$acyl with 5 to 85% of the total sum of the radicals $R_9$ and $R_{10}$ independently of one another being hydrogen or $C_1-C_8$alkyl and the remaining radicals $R_9$ and $R_{10}$ being $C_1-C_{20}$acyl;

c) a product mixture of the formula

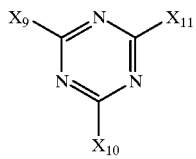
(V)

in which
$X_9$, $X_{10}$ and $X_{11}$ independently of one another are a group of the formula (III) with 5 to 85% of the total sum of the radicals $R_9$ and $R_{10}$ independently of one another being hydrogen or $C_1-C_8$alkyl and the remaining radicals $R_9$ and $R_{10}$ being $C_1-C_{20}$acyl;

d)

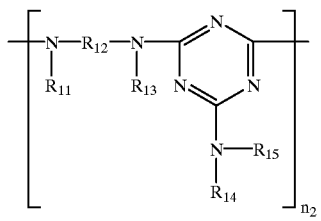
(VI)

in which
$R_{11}$, $R_{13}$, $R_{14}$ and $R_{15}$ independently of one another are hydrogen, $C_1-C_{12}$alkyl, $C_5-C_{12}$cycloalkyl, $C_1-C_4$alkyl-substituted $C_5-C_{12}$cycloalkyl, phenyl, —OH— and/or $C_1-C_{10}$alkyl-substituted phenyl, $C_7-C_9$phenylalkyl, $C_7-C_9$phenylalkyl which is substituted on the phenyl radical by —OH and/or $C_1-C_{10}$alkyl; or a group of the formula (IV),
$R_{12}$ is $C_2-C_{18}$alkylene, $C_5-C_7$cycloalkylene or $C_1-C_4$alkylenedi($C_5-C_7$cycloalkylene), or the radicals $R_{11}$, $R_{12}$ and $R_{13}$, together with the nitrogen atoms to which they are attached, form a 5- to 10-membered heterocyclic ring, or
$R_{14}$ and $R_{15}$, together with the nitrogen atom to which they are attached, form a 5- to 10-membered heterocyclic ring,
$n_2$ is a number from 2 to 50, and
at least one of the radicals $R_{11}$, $R_{13}$, $R_{14}$ and $R_{15}$ is a group of the formula (IV) with 5 to 85% of the radicals $R_{10}$ independently of one another being hydrogen or $C_1-C_8$alkyl and the remaining radicals $R_{10}$ being $C_1-C_{20}$acyl;

e)

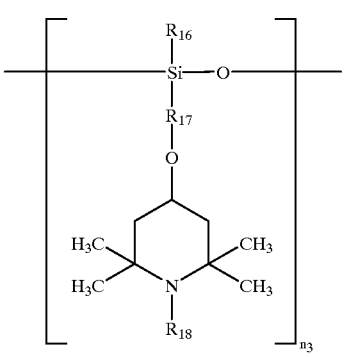
(VII)

in which
$R_{16}$ is $C_1-C_{10}$alkyl, $C_5-C_{12}$cycloalkyl, $C_1-C_4$alkyl-substituted $C_5-C_{12}$cycloalkyl, phenyl or $C_1-C_{10}$alkyl-substituted phenyl,
$R_{17}$ is $C_3-C_{10}$alkylene, the radicals $R_{18}$ independently of one another are hydrogen, $C_1-C_8$alkyl or $C_1-C_{20}$acyl with 5 to 85% of the radicals $R_{18}$ independently of one another being hydrogen or $C_1-C_8$alkyl and the remaining radicals $R_{18}$ being $C_1-C_{20}$acyl, and
$n_3$ is a number from 2 to 50;

f) a product obtainable by reacting a compound, obtained by reaction between a polyamine of the formula (VIIIa) and cyanuric chloride, with a compound of the formula (VIIIb) or a mixture of the compounds (VIIIb) and (VIIIb*) to give an intermediate

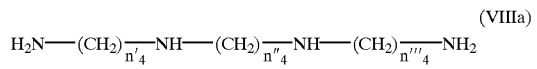
(VIIIa)

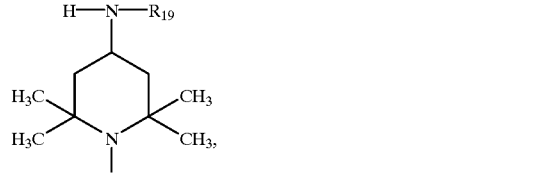
(VIIIb)

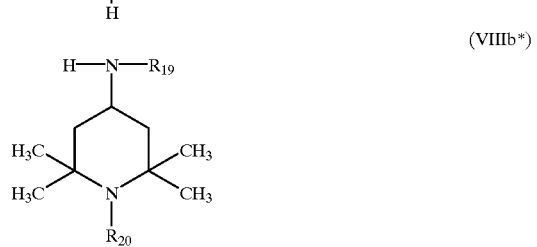
(VIIIb*)

in which
$n'_4$, $n''_4$ and $n'''_4$ independently of one another are an integer from 2 to 12,
$R_{19}$ is hydrogen, $C_1-C_{12}$alkyl, $C_5-C_{12}$cycloalkyl, phenyl or $C_7-C_9$phenylalkyl, and
$R_{20}$ is $C_1-C_8$alkyl,
with the proviso that in the mixture of the compounds (VIIIb) and (VIIIb*) at least 15% of the compound (VIIIb) is present; and subsequent acylation of the groups of the formula (A-1-a) being present in the intermediate

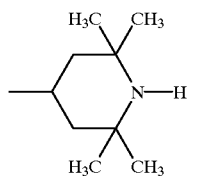
(A-1-a)

in a proportion to give a product which contains 15 to 95% of the groups of the formula (A-2)

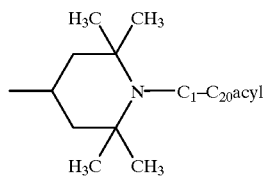
(A-2)

and 5 to 85% of the groups of the formula (A-1-a) and/or (A-1-b),

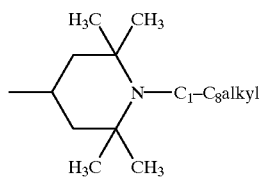
(A-1-b)

relative to the total sum of the groups (A-1-a), (A-1-b) and (A-2);

g)

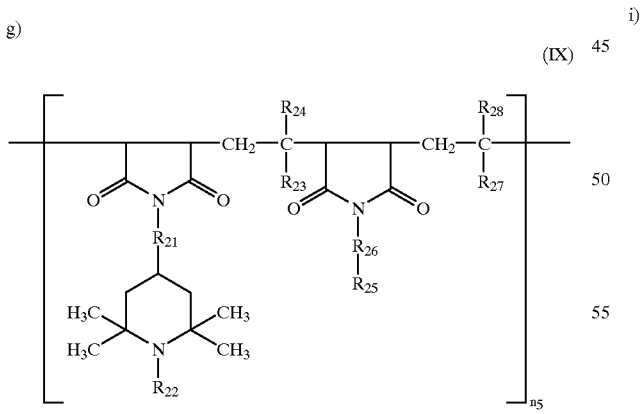
(IX)

in which
$R_{21}$ and $R_{26}$ independently of one another are a direct bond or a group —N($Y_1$)—CO—$Y_2$—CO—N($Y_3$)—,
$Y_1$ and $Y_3$ independently of one another are hydrogen, $C_1$–$C_8$alkyl, $C_5$–$C_{12}$cycloalkyl, phenyl, $C_7$–$C_9$phenylalkyl or a group of the formula (IV), $Y_2$ is a direct bond or $C_1$–$C_4$alkylene, the radicals $R_{22}$ independently of one another are hydrogen, $C_1$–$C_8$alkyl or $C_1$–$C_{20}$acyl, $R_{23}$, $R_{24}$, $R_{27}$ and $R_{28}$ independently of one another are hydrogen, $C_1$–$C_{30}$alkyl, $C_5$–$C_{12}$cycloalkyl or phenyl, $R_{25}$ is hydrogen, $C_1$–$C_{30}$alkyl, $C_5$–$C_{12}$cycloalkyl, phenyl, $C_7$–$C_9$phenylalkyl or a group of the formula (IV) with 5 to 85% of the total sum of the radicals $R_{10}$ and $R_{22}$ independently of one another being hydrogen or $C_1$–$C_8$alkyl and the remaining radicals $R_{10}$ and $R_{22}$ being $C_1$–$C_{20}$acyl, and $n_5$ is a number from 2 to 50;

h) a product mixture of the formula

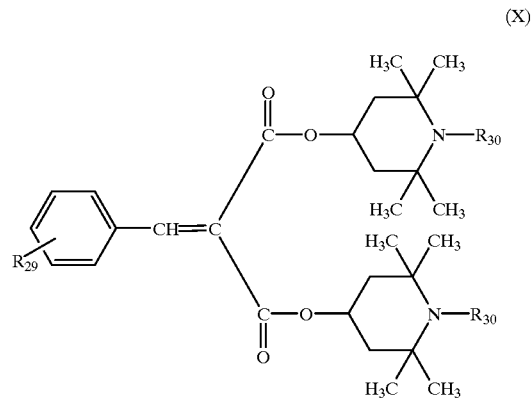
(X)

in which
$R_{29}$ is hydrogen, $C_1$–$C_{12}$alkyl or $C_1$–$C_{12}$alkoxy, and the radicals $R_{30}$ independently of one another are hydrogen, $C_1$–$C_8$alkyl or $C_1$–$C_{20}$acyl with 5 to 85% of the total sum of the radicals $R_{30}$ independently of one another being hydrogen or $C_1$–$C_8$alkyl and the remaining radicals $R_{30}$ being $C_1$–$C_{20}$acyl;

i)

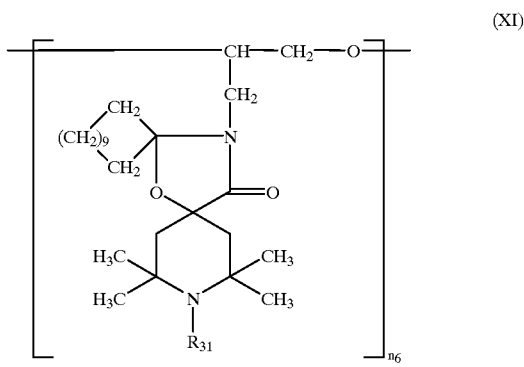
(XI)

in which
the radicals $R_3$, independently of one another are hydrogen, $C_1$–$C_8$alkyl or $C_1$–$C_{20}$acyl with 5 to 85% of the radicals $R_{31}$ independently of one another being hydrogen or $C_1$–$C_8$alkyl and the remaining radicals $R_{31}$, being $C_1$–$C_{20}$acyl, and $n_6$ is a number from 2 to 50;

j) a product mixture of the formula

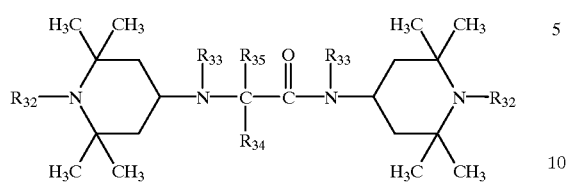

(XII)

in which
the radicals $R_{32}$ independently of one another are hydrogen, $C_1$–$C_8$alkyl or $C_1$–$C_{20}$acyl with 5 to 85% of the total sum of the radicals $R_{32}$ independently of one another being hydrogen or $C_1$–$C_8$alkyl and the remaining radicals $R_{32}$ being $C_1$–$C_{20}$acyl,
the radicals $R_{33}$ independently of one another are hydrogen, $C_1$–$C_{12}$alkyl or $C_1$–$C_{12}$acyl, and
$R_{34}$ and $R_{35}$ independently of one another are $C_1$–$C_{12}$alkyl;

k)

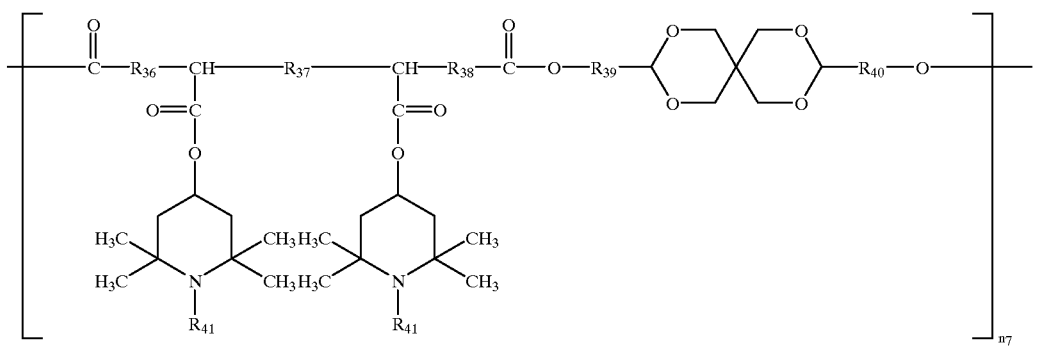

(XIII)

in which
$R_{36}$, $R_{37}$, $R_{38}$, $R_{39}$ and $R_{40}$ independently of one another are a direct bond or $C_1$–$C_{10}$alkylene, the radicals $R_{41}$ independently of one another are hydrogen, $C_1$–$C_8$alkyl or $C_1$–$C_{20}$acyl with 5 to 85% of the radicals $R_{41}$ independently of one another being hydrogen or $C_1$–$C_8$alkyl and the remaining radicals $R_{41}$ being $C_1$–$C_{20}$acyl, and
$n_7$ is a number from 1 to 50;

l) a product mixture of the formula

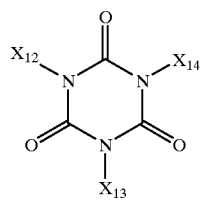

(XIV)

in which
$X_{12}$, $X_{13}$ and $X_{14}$ independently of one another are a group of the formula (XV), $$-CH_2-\underset{\underset{OH}{|}}{CH}-CH_2-A$$

(XV)

in which A is a group of the formula (III) with 5 to 85% of the total sum of the radicals $R_9$ and $R_{10}$ independently of one another being hydrogen or $C_1$–$C_8$alkyl and the remaining radicals $R_9$ and $R_{10}$ being $C_1$–$C_{20}$acyl;

m) a product mixture of the formula

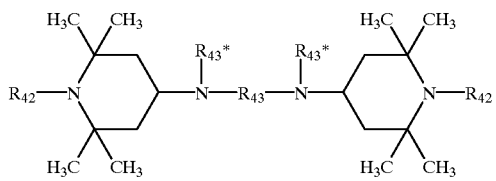

(XVI)

in which
the radicals $R_{42}$ independently of one another are hydrogen, $C_1$–$C_8$alkyl or $C_1$–$C_{20}$acyl with 5 to 85% of the total sum of the radicals $R_{42}$ independently of one another being hydrogen or $C_1$–$C_8$alkyl and the remaining radicals $R_{42}$ being $C_1$–$C_{20}$acyl,
the radicals $R_{43}$ independently of one another are $C_1$–$C_{20}$acyl, $(C_1$–$C_8$alkoxy$)$carbonyl, $(C_5$–$C_{12}$cycloalkoxy$)$carbonyl, $(C_1$–$C_8$alkyl$)$aminocarbonyl, $(C_5$–$C_{12}$cycloalkyl$)$aminocarbonyl, $(C_7$–$C_9$phenylalkyl$)$aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$, and $R_{43}$ is $C_2$–$C_{22}$alkylene, $C_5$–$C_7$cycloalkylene, $C_1$–$C_4$alkylenedi($C_5$–$C_7$cycloalkylene), phenylen phenylenedi($C_1$–$C_4$alkylene);

n) a product mixture of the formula

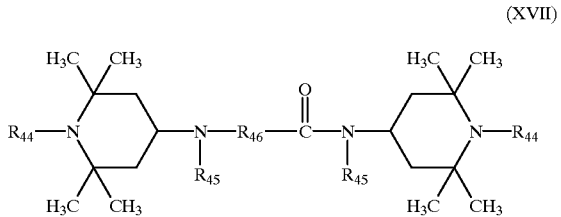

(XVII)

in which the radicals $R_{44}$ independently of one another are hydrogen, $C_1$–$C_8$alkyl or $C_1$–$C_{20}$acyl with 5 to 85% of the total sum of the radicals $R_{44}$ independently of one another being hydrogen or $C_1$–$C_8$alkyl and the remaining radicals $R_{44}$ being $C_1$–$C_{20}$acyl, the radicals $R_{45}$ independently of one another are hydrogen, $C_1$–$C_{12}$alkyl or $C_1$–$C_{12}$acyl, and $R_{46}$ is $C_1$–$C_{10}$alkylene;

o) a product mixture of the formula

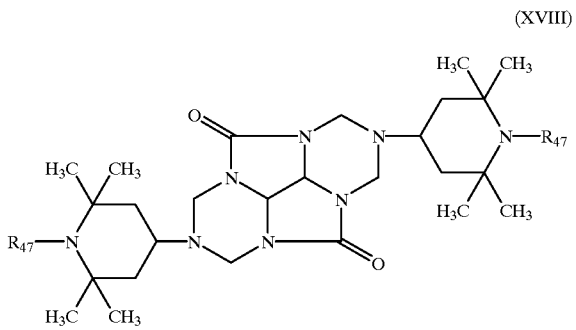

(XVIII)

in which the radicals $R_{47}$ independently of one another are hydrogen, $C_1$–$C_8$alkyl or $C_1$–$C_{20}$acyl with 5 to 85% of the total sum of the radicals $R_{47}$ independently of one another being hydrogen or $C_1$–$C_8$alkyl and the remaining radicals $R_{47}$ being $C_1$–$C_{20}$acyl; or

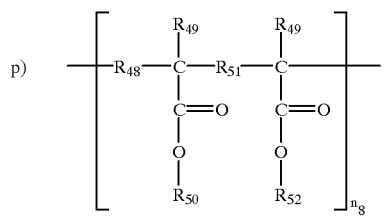

(XIX)

in which $R_{48}$ and $R_{51}$ independently of one another are $C_1$–$C_{10}$alkylene, the radicals $R_{49}$ independently of one another are hydrogen or $C_1$–$C_{10}$alkyl, $R_{50}$ is $C_1$–$C_{10}$alkyl, $R_{52}$ is $C_1$–$C_{10}$alkyl or a group of the formula (IV), and $n_8$ is a number from 3 to 50, with the proviso that at least 50% of the radicals $R_{52}$ are a group of the formula (IV) with 5 to 85% of the radicals $R_{10}$ independently of one another being hydrogen or $C_1$–$C_8$alkyl and the remaining radicals $R_{10}$ being $C_1$–$C_{20}$acyl.

Examples of alkyl having up to 30 carbon atoms are methyl, ethyl, propyl, isopropyl, n-butyl, sec-butyl, isobutyl, tert-butyl, 2-ethylbutyl, n-pentyl, isopentyl, 1-methylpentyl, 1,3-dimethyl-butyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl, docosyl and triacontyl. One of the preferred meanings of $R_{23}$ and $R_{27}$ is $C_1$–$C_{25}$alkyl, especially $C_{15}$–$C_{25}$alkyl, for example hexadecyl and $C_{18}$–$C_{22}$alkyl. One of the preferred meanings of $R_{25}$ is $C_1$–$C_{25}$alkyl, especially octadecyl. One of the preferred meanings of $R_8$ and $R_{19}$ is $C_1$–$C_4$alkyl, especially n-butyl.

Examples of $C_1$–$C_4$alkoxy are methoxy, ethoxy, propoxy and butoxy.

Examples of $C_3$–$C_6$alkenyl are allyl, 2-methallyl, butenyl, pentenyl and hexenyl. Allyl is preferred. The carbon atom in position 1 is preferably saturated.

Examples of $C_5$–$C_{12}$cycloalkyl are cyclopentyl, cyclohexyl, cycloheptyl, cyclooctyl and cyclododecyl. $C_5$–$C_8$cycloalkyl, especially cyclohexyl, is preferred.

$C_1$–$C_4$alkyl-substituted $C_5$–$C_{12}$cycloalkyl is for example methylcyclohexyl or dimethylcyclohexyl.

—OH— and/or $C_1$–$C_{10}$alkyl-substituted phenyl is for example methylphenyl, dimethylphenyl, trimethylphenyl, tert-butylphenyl or 3,5-di-tert-butyl-4-hydroxyphenyl.

Examples of $C_7$–$C_9$phenylalkyl are benzyl and phenylethyl.

$C_7$–$C_9$phenylalkyl which is substituted on the phenyl radical by —OH and/or by alkyl having up to 10 carbon atoms is, for example, methylbenzyl, dimethylbenzyl, trimethylbenzyl, tert-butylbenzyl or 3,5-di-tert-butyl-4-hydroxybenzyl.

$C_1$–$C_{20}$acyl (e.g. $C_2$–$C_{20}$acyl) is preferably $C_1$–$C_{20}$alkanoyl or $C_2$–$C_{20}$alkanoyl, $C_3$–$C_{20}$alkenoyl or benzoyl. Examples are formyl, acetyl, propionyl, butyryl, pentanoyl, hexanoyl, octanoyl, benzoyl, acryloyl and crotonoyl. $C_1$–$C_{10}$acyl (e.g. $C_2$–$C_{10}$acyl), in particular $C_1$–$C_8$acyl or $C_2$–$C_8$acyl such as $C_1$–$C_8$alkanoyl or $C_2$–$C_8$alkanoyl, $C_3$–$C_8$alkenoyl or benzoyl, especially acetyl, is preferred.

Examples of ($C_1$–$C_8$alkoxy)carbonyl are methoxycarbonyl, ethoxycarbonyl, propoxycarbonyl, butoxycarbonyl, pentoxycarbonyl, hexoxycarbonyl, heptoxycarbonyl and octoxycarbonyl. One of the preferred meanings of A is ($C_1$–$C_2$alkoxy)carbonyl.

A particularly preferred example of ($C_5$–$C_{12}$cycloalkoxy)carbonyl is cyclohexoxycarbonyl.

Examples of ($C_1$–$C_8$alkyl)aminocarbonyl are methylaminocarbonyl, ethylaminocarbonyl, propylaminocarbonyl, butylaminocarbonyl, pentylaminocarbonyl, hexylaminocarbonyl, heptylaminocarbonyl and octylaminocarbonyl. ($C_1$–$C_4$alkyl)aminocarbonyl is preferred.

A particularly preferred example of ($C_5$–$C_{12}$cycloalkyl)aminocarbonyl is cyclohexylaminocarbonyl.

A particularly preferred example of ($C_7$–$C_9$phenylalkyl)aminocarbonyl is benzylaminocarbonyl.

Examples of alkylene having up to 22 carbon atoms are methylene, ethylene, propylene, trimethylene, tetramethylene, pentamethylene, 2,2-dimethyltrimethylene, hexamethylene, trimethylhexamethylene, octamethylene and decamethylene. $R_{12}$ is preferably hexamethylene, $R_{36}$ and $R_{38}$ are preferably methylene, $R_{39}$ is preferably 2,2-dimethylethylene and $R_{40}$ 1,1-dimethylethylene.

An example of $C_4$–$C_{10}$alkanetetrayl is 1,2,3,4-butanetetrayl.

An example of bis{($C_1$–$C_{20}$alkyl)oxycarbonyl}$C_4$–$C_{10}$alkanetetrayl is bis{tridecyloxycarbonyl}butanetetrayl.

An example of $C_5$–$C_7$cycloalkylene is cyclohexylene.

An example of $C_1$–$C_4$alkylenedi($C_5$–$C_7$-cycloalkylene) is methylenedicyclohexylene.

An example of phenylenedi($C_1$–$C_4$alkylene) is phenylenedimethylene.

Where the radicals $R_{11}$, $R_{12}$ and $R_{13}$, together with the nitrogen atoms to which they are attached, form a 5- to 10-membered heterocyclic ring, the resulting ring is for example

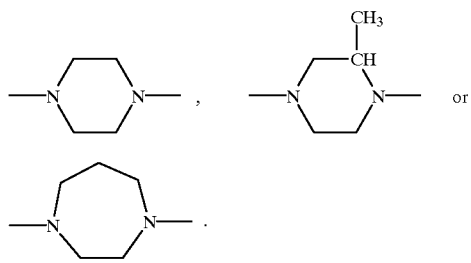

A 6-membered heterocyclic ring is preferred.

Where the radicals $R_{14}$ and $R_{15}$, together with the nitrogen atom to which they are attached, form a 5- to 10-membered heterocyclic ring, the resulting ring is for example 1-pyrrolidyl, piperidino, morpholino, 1-piperazinyl, 4-methyl-1-piperazinyl, 1-hexahydroazepinyl, 5,5,7-trimethyl-1-homopiperazinyl or 4,5,5,7-tetramethyl-1-homopiperazinyl. Morpholino is particularly preferred.

One of the preferred meanings of $R_{23}$ and $R_{27}$ is phenyl.

$Y_2$ and $R_{37}$ are preferably a direct bond.

One of the preferred meanings of $Y_1$ and $Y_3$ is hydrogen.

A preferred meaning of the group

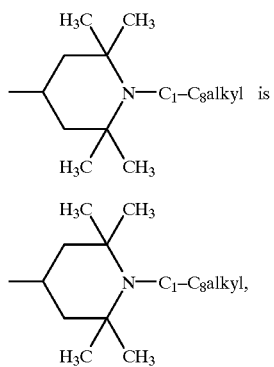

in particular

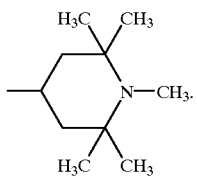

$n_2$ is preferably 2–25.

$n_3$ is preferably 2–25, especially 2–20 or 2–10.

$n_4'$, $n_4''$ and $n_4'''$ are preferably 2–4.

$n_5$ is preferably 2–25, especially 2–20 or 2–10.

$n_6$ is preferably 2–25, especially 2–20 or 2–10.

$n_7$ is preferably 1–25, especially 1–20 or 1–10.

$n_8$ is preferably 3–25, especially 3–20.

A product which is of interest is one wherein $n_1$ is 2 or 4, if $n_1$ is 2, $R_2$ is $C_2$–$C_{10}$alkylene or bis{$C_1$–$C_{15}$alkyl}oxycarbonyl, and if $n_1$ is 4, $R_2$ is 1,2,3,4-butanetetrayl;

$R_3$ and $R_7$ independently of one another are hydrogen, $C_1$–$C_4$alkyl or $C_1$–$C_{20}$acyl, $R_4$, $R_5$ and $R_6$ independently of one another are $C_2$–$C_6$alkylene, and $R_8$ is hydrogen, $C_1$–$C_6$alkyl, $C_5$–$C_8$cycloalkyl, methyl-substituted $C_5$–$C_8$cycloalkyl, phenyl, $C_7$–$C_9$phenylalkyl or a group of the formula (IV);

$R_{11}$, $R_{13}$, $R_{14}$ and $R_{15}$ independently of one another are hydrogen, $C_1$–$C_8$alkyl, $C_5$–$C_8$cycloalkyl, methyl-substituted $C_5$–$C_8$cycloalkyl, phenyl, $C_7$–$C_9$phenylalkyl or a group of the formula (IV), or the radicals $R_{14}$ and $R_{15}$, together with the nitrogen atom to which they are attached, form a 6-membered heterocyclic ring, $R_{12}$ is $C_2$–$C_{10}$alkylene, and $n_2$ is a number from 2 to 25;

$R_{16}$ is $C_1$–$C_4$alkyl, $C_5$–$C_8$cycloalkyl or phenyl, $R_{17}$ is $C_3$–$C_6$alkylene, and $n_3$ is a number from 2 to 25;

$n'_4$, $n''_4$ and $n'''_4$ independently of one another are an integer from 2 to 4, and $R_{19}$ is $C_1$–$C_4$alkyl;

$R_{21}$ and $R_{26}$ independently of one another are a direct bond or a group —N($Y_1$)—CO—$Y_2$—CO—N($Y_3$)—, $Y_1$ and $Y_3$ independently of one another are hydrogen or $C_1$–$C_4$alkyl, $Y_2$ is a direct bond, $R_{23}$ and $R_{27}$ are $C_1$–$C_{25}$alkyl or phenyl, $R_{24}$ and $R_{28}$ are hydrogen or $C_1$–$C_4$alkyl,
$R_{25}$ is $C_1$–$C_{25}$alkyl or a group of the formula (IV), and
$n_5$ is a number from 2 to 25;
$R_{29}$ is hydrogen, $C_1$–$C_4$alkyl or $C_1$–$C_4$alkoxy;
$n_6$ is a number from 2 to 25;
the radicals $R_{33}$ independently of one another are hydrogen or $C_1$–$C_4$alkyl, and
the radicals $R_{34}$ and $R_{35}$ independently of one another are $C_1$–$C_4$alkyl;
$R_{36}$, $R_{38}$, $R_{39}$ and $R_{40}$ independently of one another are $C_1$–$C_4$alkylene,
$R_{37}$ is a direct bond, and
$n_7$ is a number from 1 to 25;
$R_{43}$ is $C_2$–$C_6$alkylene, cyclohexylene or phenylene;
the radicals $R_{45}$ independently of one another are hydrogen or $C_1$–$C_4$alkyl, and
$R_{46}$ is $C_2$–$C_6$alkylene; and
$R_{48}$ and $R_{51}$ independently of one another are $C_1$–$C_6$alkylene,
the radicals $R_{49}$ independently of one another are hydrogen or $C_1$–$C_4$alkyl,
$R_{50}$ is $C_1$–$C_4$alkyl,
$R_{52}$ is $C_1$–$C_4$alkyl or a group of the formula (IV), and
$n_8$ is a number from 3 to 25.

A product which relates to a preferred embodiment is one corresponding
a) to a product mixture of the formula

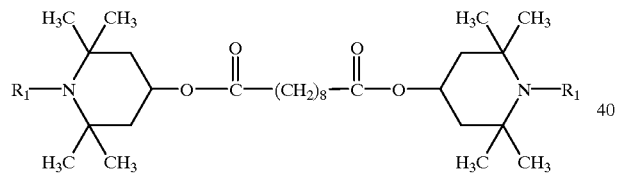

(I-a)

wherein 5 to 85% of the total sum of the radicals $R_1$ are hydrogen or methyl and the remaining radicals $R_1$ are $C_1$–$C_{10}$acyl;
to a product mixture of the formula wherein 5 to 85% of the total sum of the radicals $R_1$ are hydrogen or methyl and the remaining radicals $R_1$ are $C_1$–$C_{10}$acyl; or
to a product mixture of the formula

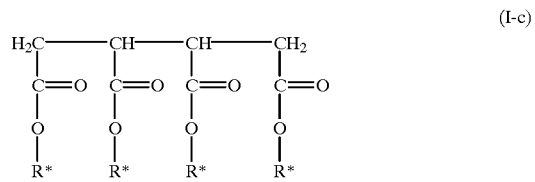

(I-c)

wherein two of the radicals R* are —COO—$C_{13}H_{27}$, and
two of the radicals R* are a group

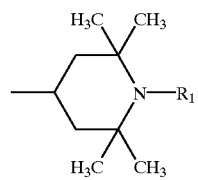

with 5 to 85% of the total sum of the radicals $R_1$ being hydrogen or methyl and the remaining radicals $R_1$ being $C_1$–$C_{10}$acyl;

b) to a product mixture of the formula (II-a)

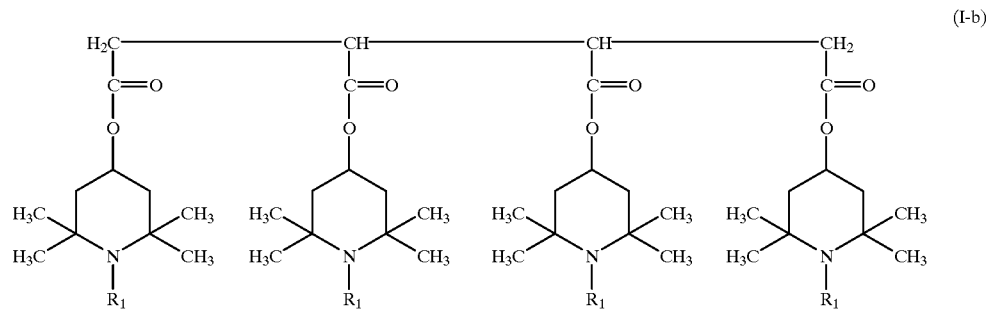

(I-b)

(II-a)
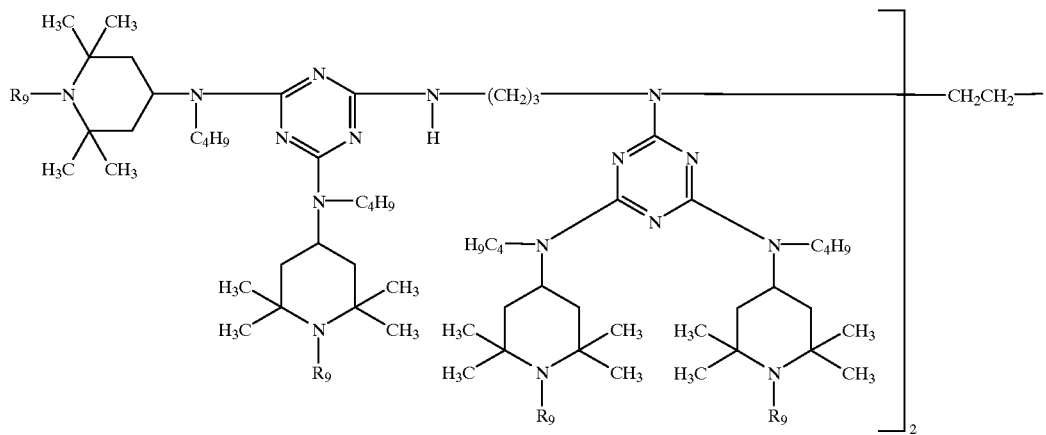
wherein 5 to 85% of the total sum of the radicals $R_9$ are hydrogen or methyl and the remaining radicals $R_9$ are $C_1$–$C_{10}$acyl;
c) to a product mixture of the formula (V-a)
(V-a)
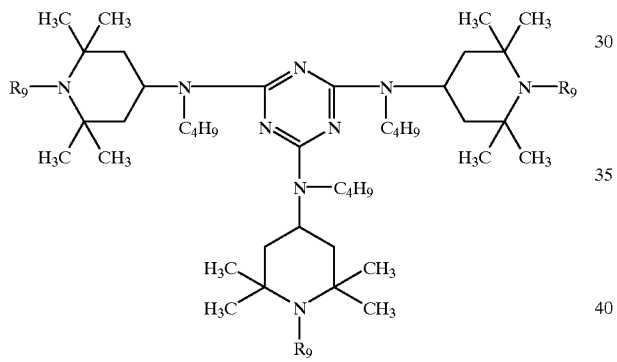
wherein 5 to 85% of the total sum of the radicals $R_9$ are hydrogen or methyl and the remaining radicals $R_9$ are $C_1$–$C_{10}$acyl;
d) to the formula (VI-a), (VI-b), (VI-c), (VI-d) or (VI-e)
(VI-a)
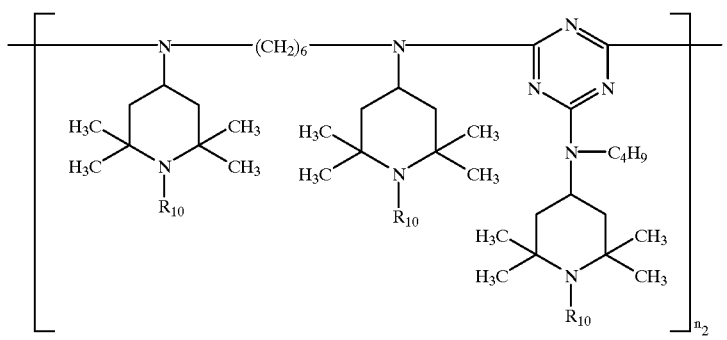

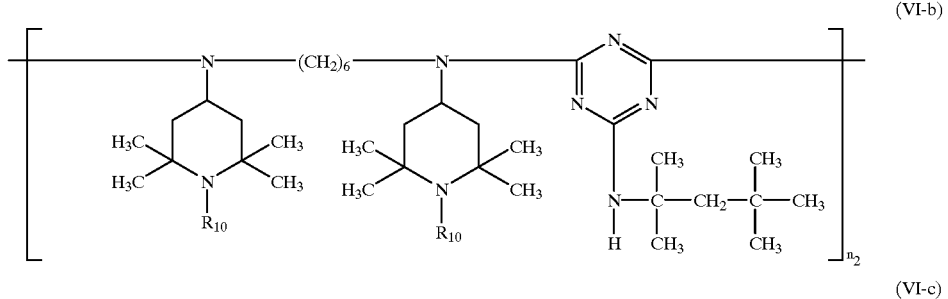
(VI-b)
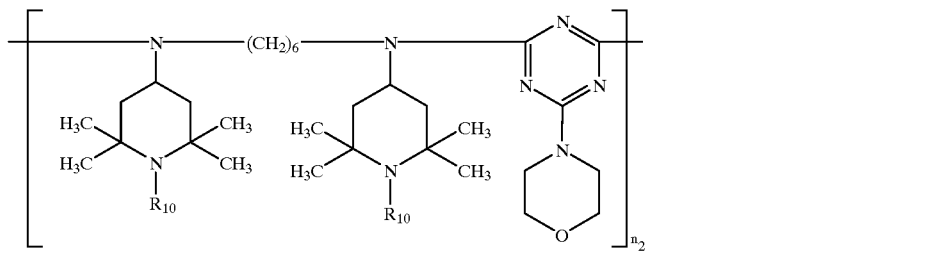
(VI-c)
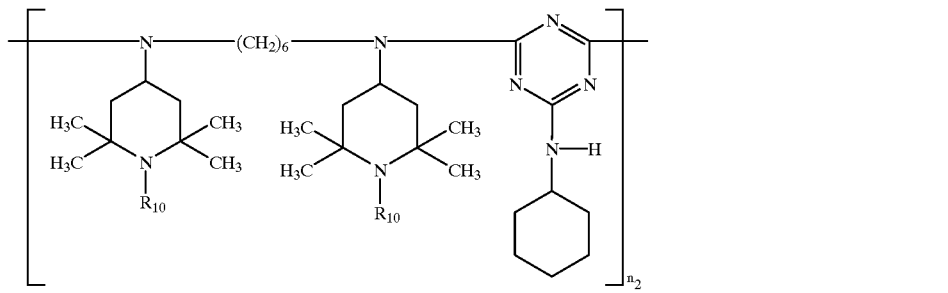
(VI-d)
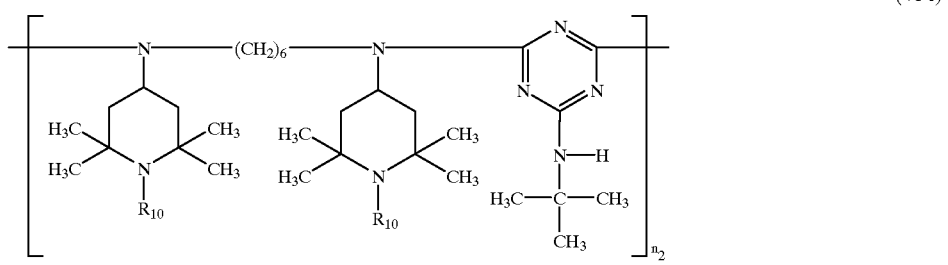
(VI-e)
wherein 5 to 85% of the radicals $R_{10}$ independently of one another are hydrogen or methyl and the remaining radicals $R_{10}$ are $C_1$-$C_{10}$acyl;
e) to the formula (VII-a)
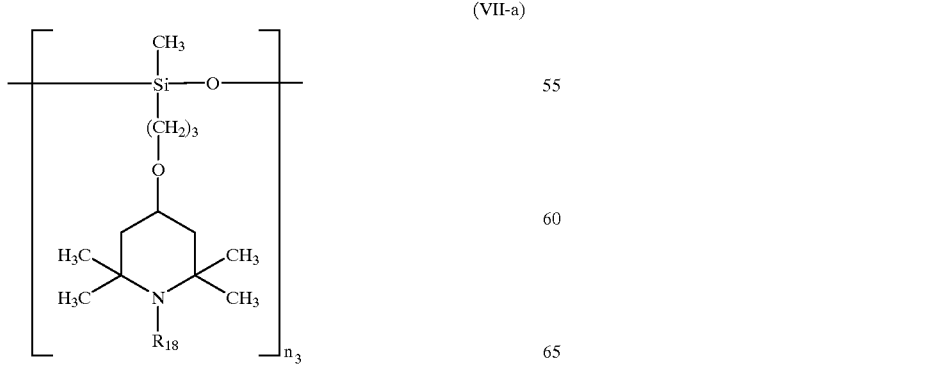
(VII-a)

wherein 5 to 85% of the radicals $R_{18}$ independently of one another are hydrogen or methyl and the remaining radicals $R_{18}$ are $C_1$–$C_{10}$acyl;

f) to a product obtainable by reacting a compound, obtained by reaction between a polyamine of the formula (VIIIa-1) and cyanuric chloride, with a compound of the formula (VIIIb-1) or a mixture of the compounds (VIIIb-1) and (VIIIb*-1) to give an intermediate

 (VIIa-1)

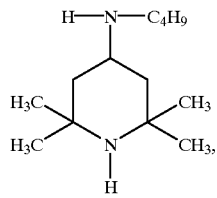 (VIIIb-1)

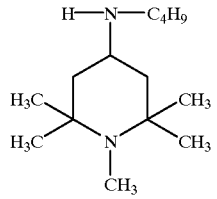 (VIIIb*-1)

with the proviso that in the mixture of the compounds (VIIIb-1) and (VIIIb*-1) at least 15% of the compound (VIIIb-1) is present;
and subsequent acylation of the groups of the formula (A-1-a) being present in the intermediate

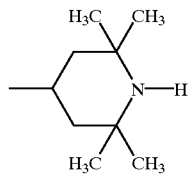 (A-1-a)

in a proportion to give a product which contains 15 to 95% of the groups of the formula (A-2-1)

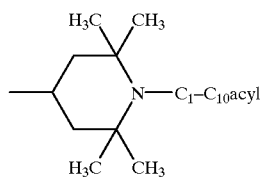 (A-2-1)

and 5 to 85% of the groups of the formula (A-1-a) and or (A-1-b-1),

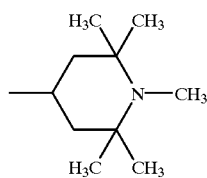 (A-1-b-1)

relative to the total sum of the groups (A-1-a), (A-1-b-1) and (A-2-1);

g) to the formula (IX-a), (IX-b) or (IX-c)

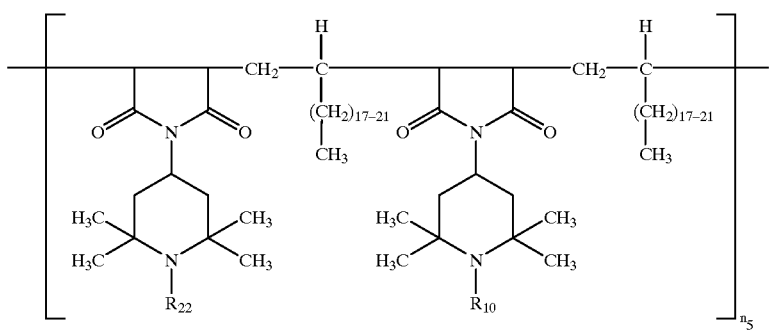 (IX-a)

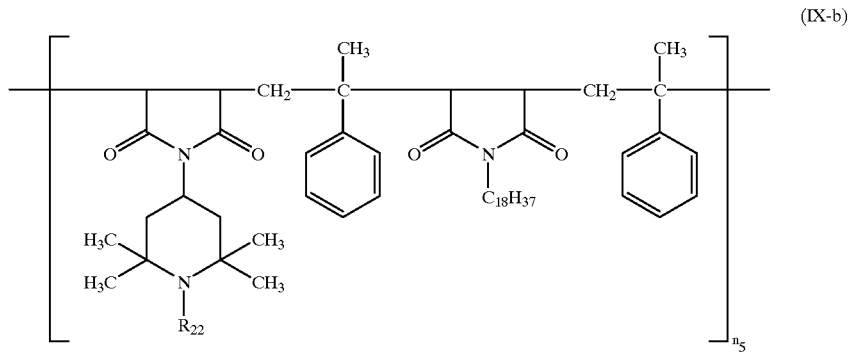

(IX-b)

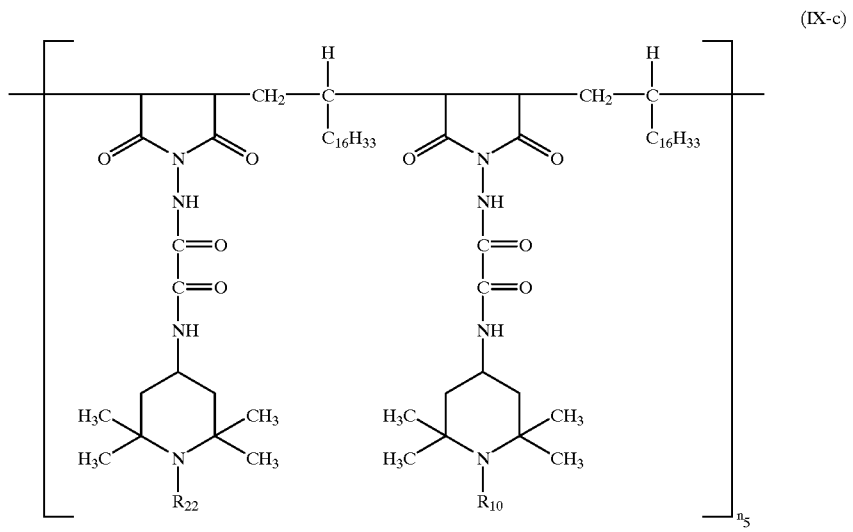

(IX-c)

wherein 5 to 85% of the radicals $R_{10}$ and $R_{22}$ independently of one another are hydrogen or methyl and the remaining radicals $R_{10}$ and $R_{22}$ are $C_1$–$C_{10}$acyl;

h) to a product mixture of the formula (X-a)

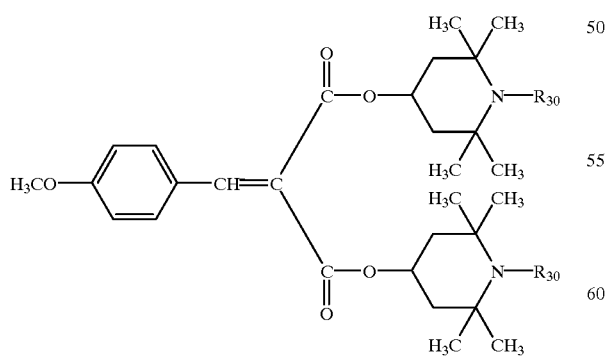

(X-a)

wherein 5 to 85% of the total sum of the radicals $R_{31}$ are hydrogen or methyl and the remaining radicals $R_{30}$ are $C_1$–$C_{10}$acyl;

i) to the formula (XI) wherein 5 to 85% of the radicals $R_{31}$ independently of one another are hydrogen or methyl and the remaining radicals $R_{31}$ are $C_1$–$C_{10}$acyl;

j) to a product mixture of the formula (XII-a)

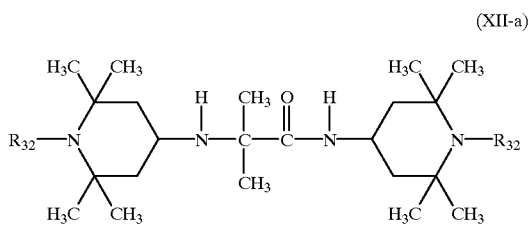

(XII-a)

wherein 5 to 85% of the total sum of the radicals $R_{32}$ are hydrogen or methyl and the remaining radicals $R_{32}$ are $C_1$–$C_{10}$acyl;

k) to the formula (XIII-a)

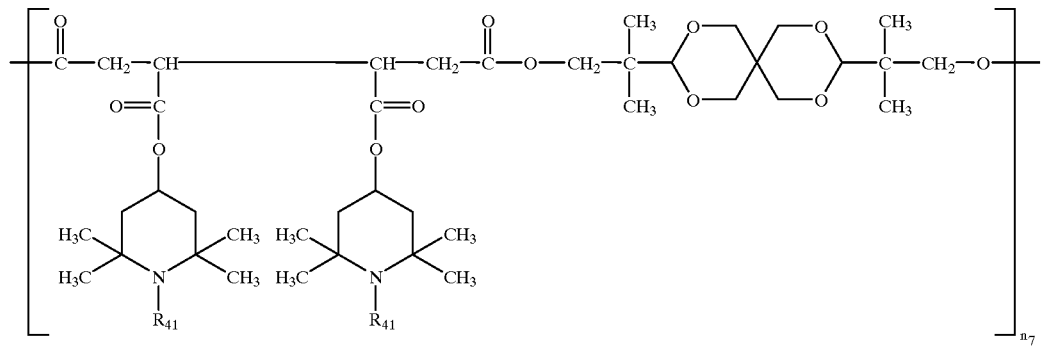

wherein 5 to 85% of the radicals $R_{41}$ independently of one another are hydrogen or methyl and the remaining radicals $R_{41}$ are $C_1$–$C_{10}$acyl;

l) to a product mixture of the formula (XIV-a)

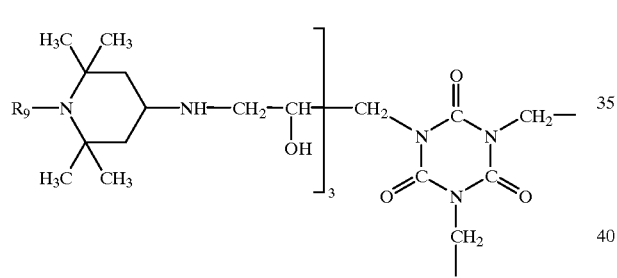

wherein 5 to 85% of the total sum of the radicals $R_9$ are hydrogen or methyl and the remaining radicals $R_9$ are $C_1$–$C_{10}$acyl;

m) to a product mixture of the formula (XVI-a)

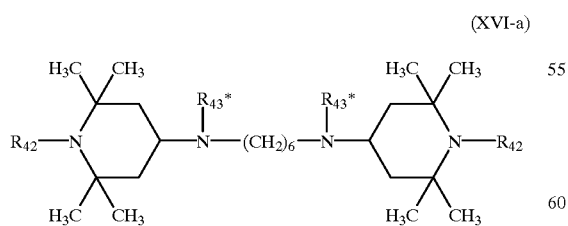

wherein 5 to 85% of the total sum of the radicals $R_{42}$ are hydrogen or methyl and the remaining radicals $R_{42}$ are $C_1$–$C_{10}$acyl; and the radicals $R_{43}$* are $C_1$–$C_{10}$acyl;

n) to a product mixture of the formula (XVII-a)

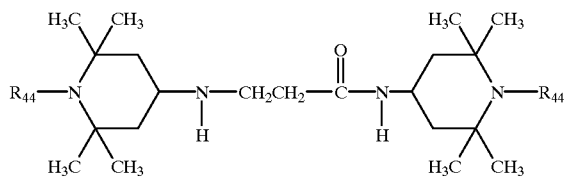

wherein 5 to 85% of the total sum of the radicals $R_{44}$ are hydrogen or methyl and the remaining radicals $R_{44}$ are $C_1$–$C_{10}$acyl;

o) to a product mixture of the formula (XVIII) wherein 5 to 85% of the total sum of the radicals $R_{47}$ are hydrogen or methyl and the remaining radicals $R_{47}$ are $C_1$–$C_{10}$acyl; or p) to the formula (XIX-a)

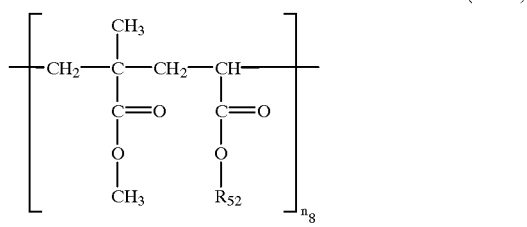

wherein the radicals $R_{52}$ independently of one another are ethyl or a group of the formula (IV), with the provisos that (1) at least 50% of the radicals $R_{52}$ are a group of the formula (IV) with $R_{10}$ being hydrogen, methyl or $C_1$–$C_{10}$acyl, and the remaining radicals $R_{52}$ are ethyl and (2) 5 to 85% of the radicals $R_{10}$ independently of one another are hydrogen or methyl and the remaining radicals $R_{10}$ are $C_1$–$C_{10}$acyl.

A product which relates to a further preferred embodiment is one corresponding a) to a product mixture of the formula (I-a)
wherein 20 to 70% of the total sum of the radicals $R_1$ are hydrogen or methyl and the remaining radicals $R_1$ are $C_1$–$C_{10}$acyl;
to a product mixture of the formula (I-b)
wherein 20 to 70% of the total sum of the radicals $R_1$ are hydrogen or methyl and the remaining radicals $R_1$ are $C_1$–$C_{10}$acyl; or
to a product mixture of the formula (I-c)
wherein 20 to 70% of the total sum of the radicals $R_1$ are hydrogen or methyl and the remaining radicals $R_1$ are $C_1$–$C_{10}$acyl;

b) to a product mixture of the formula (II-a)
wherein 20 to 70% of the total sum of the radicals $R_9$ are hydrogen or methyl and the remaining radicals $R_9$ are $C_1$–$C_{10}$acyl;

c) to a product mixture of the formula (V-a)
wherein 20 to 70% of the total sum of the radicals $R_9$ are hydrogen or methyl and the remaining radicals $R_9$ are $C_1$–$C_{10}$acyl;

d) to the formula (VI-a), (VI-b), (VI-c), (VI-d) or (VI-e)
wherein 20 to 70% of the radicals $R_{10}$ independently of one another are hydrogen or methyl and the remaining radicals $R_{10}$ are $C_1$–$C_{10}$acyl;

e) to the formula (VII-a)
wherein 20 to 70% of the radicals $R_{18}$ independently of one another are hydrogen or methyl and the remaining radicals $R_{18}$ are $C_1$–$C_{10}$acyl;

f) to a product obtainable by reacting a compound, obtained by reaction between a polyamine of the formula (VIIIa-1) and cyanuric chloride, with a compound of the formula (VIIIb-1) or a mixture of the compounds (VIIIb-1) and (VIIIb*-1) to give an intermediate with the proviso that in the mixture of the compounds (VIIIb-1) and (VIIIb*-1) at least 30% of the compound (VIIIb-1) is present;
and subsequent acylation of the groups of the formula (A-1-a) being present in the intermediate
in a proportion to give a product which contains 30 to 80% of the groups of the formula (A-2-1)
and 20 to 70% of the groups of the formula (A-1-a) and/or (A-1-b-1),
relative to the total sum of the groups (A-1-a), (A-1-b-1) and (A-2-1);

g) to the formula (IX-a), (IX-b) or (IX-c)
wherein 20 to 70% of the radicals $R_{10}$ and $R_{22}$ independently of one another are hydrogen or methyl and the remaining radicals $R_{10}$ and $R_{22}$ are $C_1$–$C_{10}$acyl;

h) to a product mixture of the formula (X-a)
wherein 20 to 70% of the total sum of the radicals $R_{30}$ are hydrogen or methyl and the remaining radicals $R_{30}$ are $C_1$–$C_{10}$acyl;

i) to the formula (XI) wherein 20 to 70% of the radicals $R_{31}$ independently of one another are hydrogen or methyl and the remaining radicals $R_{31}$ are $C_1$–$C_{10}$acyl;

j) to a product mixture of the formula (XII-a)
wherein 20 to 70% of the total sum of the radicals $R_{32}$ are hydrogen or methyl and the remaining radicals $R_{32}$ are $C_1$–$C_{10}$acyl;

k) to the formula (XIII-a)
wherein 20 to 70% of the radicals $R_{41}$ independently of one another are hydrogen or methyl and the remaining radicals $R_{41}$ are $C_1$–$C_{10}$acyl;

l) to a product mixture of the formula (XIV-a)
wherein 20 to 70% of the total sum of the radicals $R_9$ are hydrogen or methyl and the remaining radicals $R_9$ are $C_1$–$C_{10}$acyl;

m) to a product mixture of the formula (XVI-a)
wherein 20 to 70% of the total sum of the radicals $R_{42}$ are hydrogen or methyl and the remaining radicals $R_{42}$ are $C_1$–$C_{10}$acyl;

n) to a product mixture of the formula (XVII-a)
wherein 20 to 70% of the total sum of the radicals $R_{44}$ are hydrogen or methyl and the remaining radicals $R_{44}$ are $C_1$–$C_{10}$acyl;

o) to a product mixture of the formula (XVIII) wherein 20 to 70% of the total sum of the radicals $R_{47}$ are hydrogen or methyl and the remaining radicals $R_{47}$ are $C_1$–$C_{10}$acyl; or p) to the formula (XIX-a)
wherein 20 to 70% of the radicals $R_{10}$ independently of one another are hydrogen or methyl and the remaining radicals $R_{10}$ are $C_1$–$C_{10}$acyl.

A product which relates to a particular preferred embodiment is one corresponding a) to a product mixture of the formula (I-a)
wherein 15 to 30% of the total sum of the radicals $R_1$ are hydrogen or methyl and the remaining radicals $R_1$ are $C_1$–$C_{10}$acyl;

b) to a product mixture of the formula (II-a)
wherein 30 to 50% of the total sum of the radicals $R_9$ are hydrogen or methyl and the remaining radicals $R_9$ are $C_1$–$C_{10}$acyl;

d) to the formula (VI-a)
wherein 15 to 85% of the radicals $R_{10}$ independently of one another are hydrogen or methyl and the remaining radicals $R_{10}$ are $C_1$–$C_{10}$acyl; or
to the formula (VI-b) or (VI-c)
wherein 15 to 60% of the radicals $R_{10}$ independently of one another are hydrogen or methyl and the remaining radicals $R_{10}$ are $C_1$–$C_{10}$acyl;

e) to the formula (VII-a)
wherein 15 to 35% of the radicals $R_{18}$ independently of one another are hydrogen or methyl and the remaining radicals $R_{18}$ are $C_1$–$C_{10}$acyl;

f) to a product obtainable by reacting a compound, obtained by reaction between a polyamine of the formula (VIIIa-1) and cyanuric chloride, with a compound of the formula (VIIIb-1) or a mixture of the compounds (VIIIb-1) and (VIIIb*-1) to give an intermediate with the proviso that in the mixture of the compounds (VIIIb-1) and (VIIIb*-1) at least 50% of the compound (VIIIb-1) is present;
and subsequent acylation of the groups of the formula (A-1-a) being present in the intermediate
in a proportion to give a product which contains 50 to 70% of the groups of the formula (A-2-1)
and 30 to 50% of the groups of the formula (A-1-a) and/or (A-1-b-1),
relative to the total sum of the groups (A-1-a), (A-1-b-1) and (A-2-1);

k) to the formula (XIII-a)
wherein 15 to 30% of the radicals $R_{41}$ independently of one another are hydrogen or methyl and the remaining radicals $R_{41}$ are $C_1$–$C_{10}$acyl; or m) to a product mixture of the formula (XVI-a)
   wherein 30 to 50% of the total sum of the radicals $R_{42}$ are hydrogen or methyl and the remaining radicals $R_{42}$ are $C_1$–$C_{10}$acyl.

A product wherein the meaning $C_1$–$C_{10}$acyl is acetyl is especially preferred.

A product which corresponds to the formula (VI-a) wherein 40 to 60%, e.g. 25 to 50%, of the radicals $R_{10}$ independently of one another are hydrogen or methyl is also preferred.

A product which corresponds to the formula (VI-a) wherein 40 to 60%, e.g. 25 to 50%, of the radicals $R_{10}$ are hydrogen and the remaining radicals $R_{10}$ are acetyl is particularly preferred.

The products described under a) to p) above can be prepared, for example, by the method indicated below under "Example of a preparation process", using the corresponding 2,2,6,6-tetramethylpiperidine derivatives (unsubstituted nitrogen in the 2,2,6,6-tetramethyl-4-piperidyl groups) as starting compounds. The 2,2,6,6-tetramethylpiperidine derivatives are essentially known (some are commercially available) and can be prepared by known methods, for example as described in U.S. Pat. No. 3,640,928, U.S. Pat. No. 4,108,829, U.S. Pat. No. 3,925,376, U.S. Pat. No. 4,086,204, EP-A-782,994, EP-A-850,938, U.S. Pat. No. 4,331,586, U.S. Pat. No. 5,051,458, U.S. Pat. No. 4,477,615 and Chemical Abstracts—CAS No. 136504-96-6, U.S. Pat. No. 4,857,595, DD-A-262,439 (Derwent 89-122983/17, Chemical Abstracts 111:58964u), WO-A-94/12,544 (Derwent 94-177274/22), GB-A-2,269,819, U.S. Pat. No. 4,340,534, EP-A-172,413, U.S. Pat. No. 4,529,760, U.S. Pat. No. 5,182,390 (Chemical Abstracts—CAS No. 144923-25-1), U.S. Pat. No. 4,976,889, SU-A-768,175 (Derwent 88-138,751/20), U.S. Pat. No. 4,769,457 and DE-A-2,748,362 (Derwent 35517B/19).

The 2,2,6,6-tetramethylpiperidine derivative intermediate belonging to item f) above can be prepared in analogy to known methods, for example by reacting a polyamine of the formula (VIIIa) with cyanuric chloride in a molar ratio of from 1:2 to 1:4 in the presence of anhydrous lithium carbonate, sodium carbonate or potassium carbonate in an organic solvent such as 1,2-dichloroethane, toluene, xylene, benzene, dioxane or tert-amyl alcohol at a temperature of from −20° C. to +10° C., preferably from −10° C. to +10° C., in particular from 0° C. to +10° C., for from 2 to 8 hours and then reacting the resulting product with a 2,2,6,6-tetramethyl-4-piperidylamine of the formula (VIIIb). The molar ratio of 2,2,6,6-tetramethyl-4-piperidylamine to the polyamine of the formula (VIIIa) which is employed is, for example, from 4:1 to 8:1. The quantity of 2,2,6,6-tetramethyl-4-piperidylamine can be added in one go or in two or more portions at an interval of a few hours.

The ratio of polyamine of the formula (VIIIa) to cyanuric chloride to 2,2,6,6-tetramethyl-4-piperidylamine of the formula (VIIIb) is preferably from 1:3:5 to 1:3:6.

The following example indicates a possible method of preparing the preferred 2,2,6,6-tetramethylpiperidine derivative intermediate which belongs to item f) above.

EXAMPLE 23.6 g (0.128 mol) of cyanuric chloride, 7.43 g (0.0426 mol) of N,N'-bis[3-aminopropyl]ethylenediamine and 18 g (0.13 mol) of anhydrous potassium carbonate are reacted in 250 ml of 1,2-dichloroethane at 5° C. for 3 hours with stirring. The mixture is heated at room temperature for a further 4 hours. 27.2 g (0.128 mol) of N-(2,2,6,6-tetramethyl-4-piperidyl)butylamine are added and the mixture obtained is heated at 60° C. for 2 hours. A further 18 g (0.13 mol) of anhydrous potassium carbonate are added and the mixture is heated at 60° C. for a further 6 hours. The solvent is distilled off under a slight vacuum (200 mbar) and replaced by xylene. 18.2 g (0.085 mol) of N-(2,2,6,6-tetramethyl-4-piperidyl)butylamine and 5.2 g (0.13 mol) of ground sodium hydroxide are added and the reaction mixture is heated at reflux for 2 hours, and for a further 12 hours, the water produced in the reaction is removed by azeotropic distillation. The mixture is filtered. The solution is washed with water and dried over $Na_2SO_4$. The solvent is evaporated off and the residue is dried in vacuo (0.1 mbar) at 120–130° C. The desired product is obtained as a colourless resin.

In general, a 2,2,6,6-tetramethylpiperidine derivative intermediate belonging to item f) above can be represented, for example, by a compound of the formula (VIII-1), (VIII-2) or (VIII-3). It can also be present as a mixture of these three compounds.

(VIII-1)

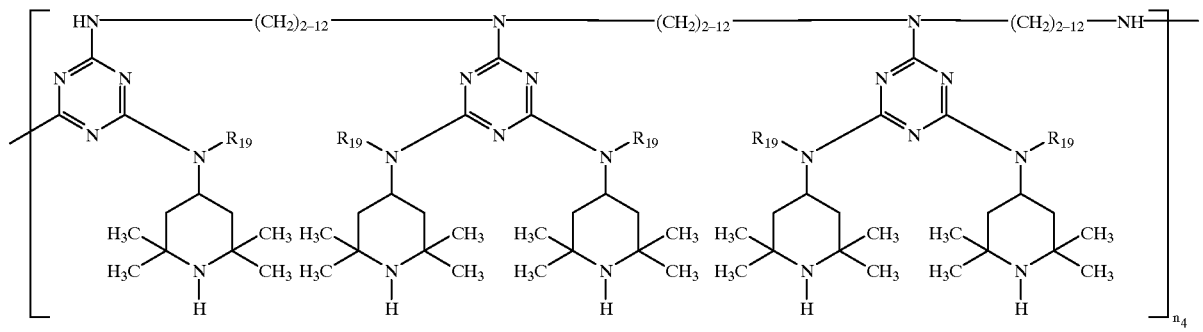

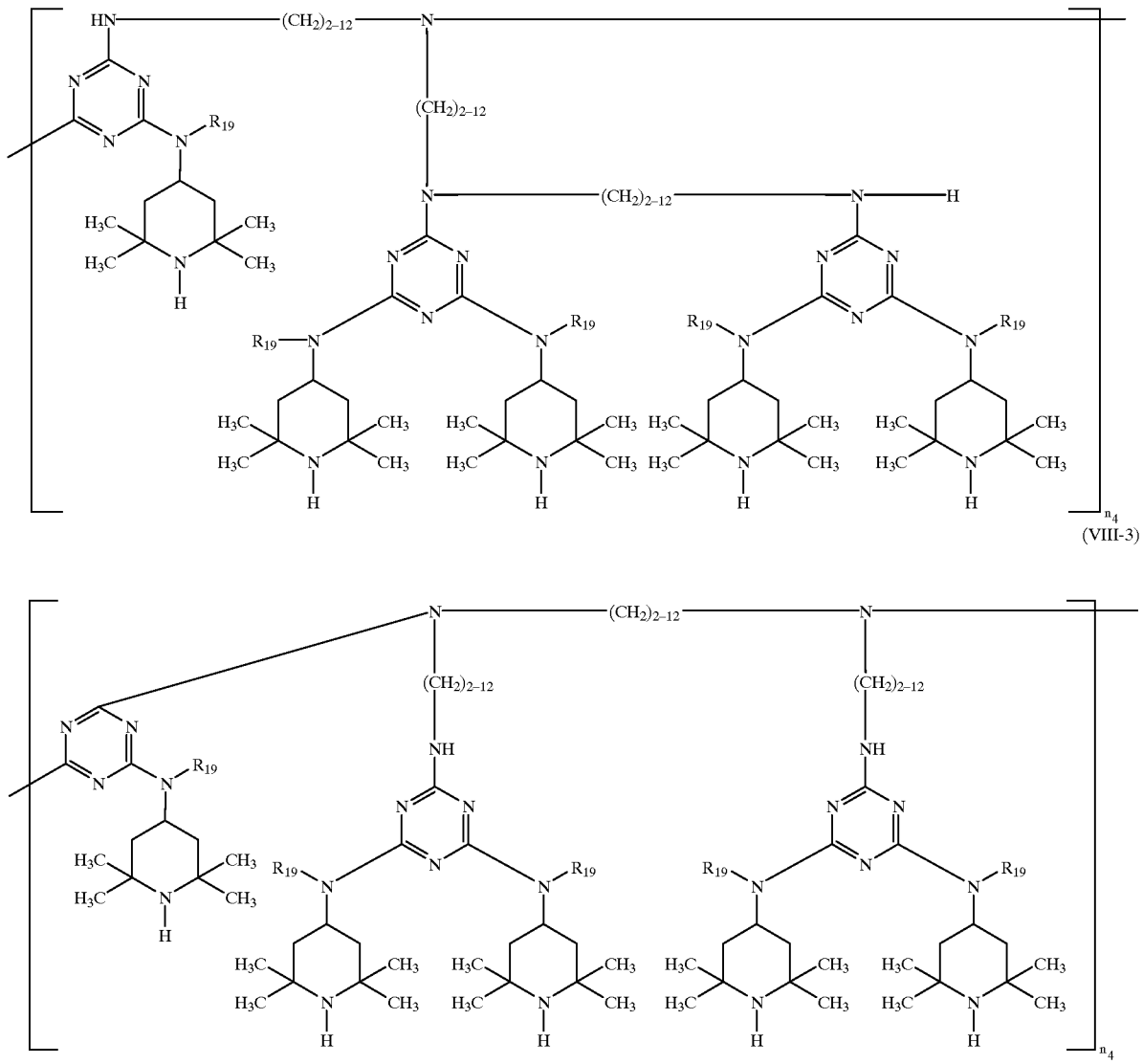
(VIII-2)
(VIII-3)
A preferred meaning of the formula (VIII-1) is
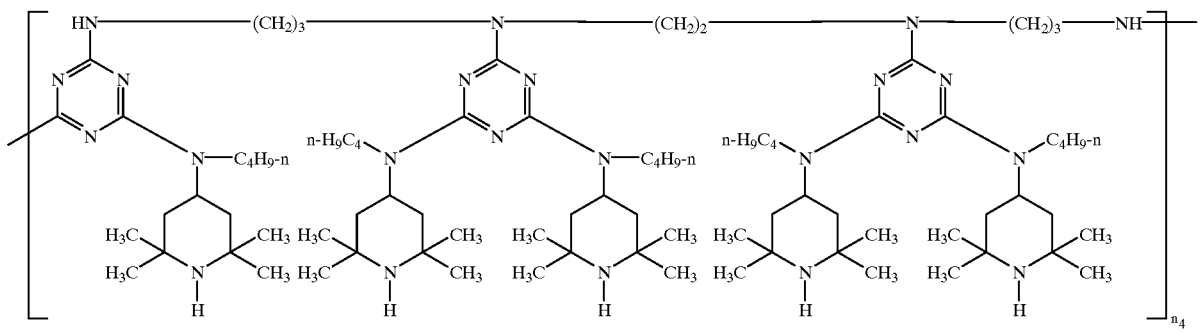

A preferred meaning of the formula (VIII -2) is

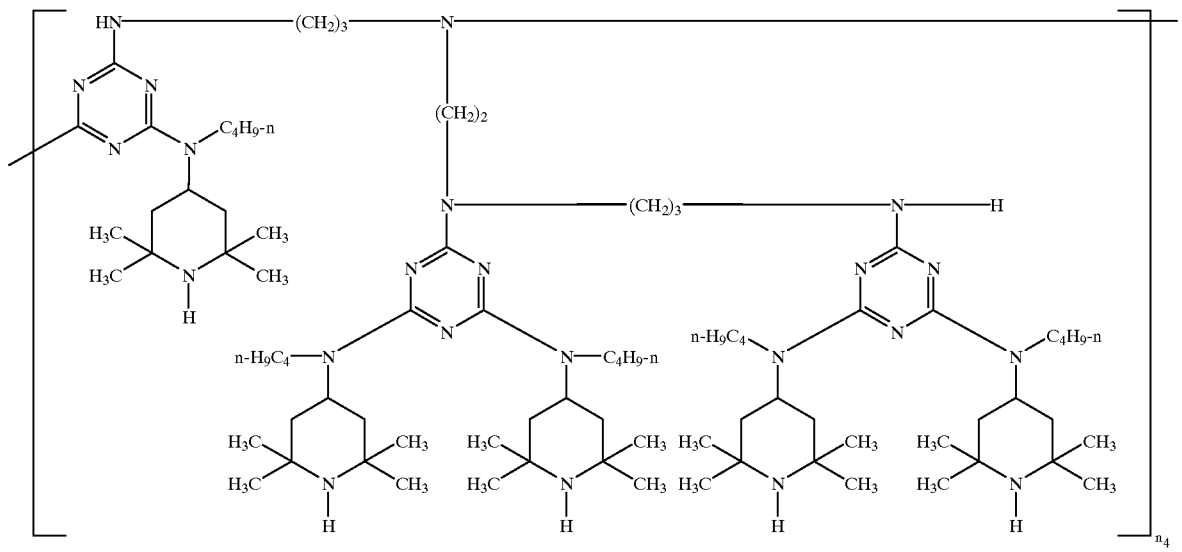

A preferred meaning of the formula (VIII-3) is

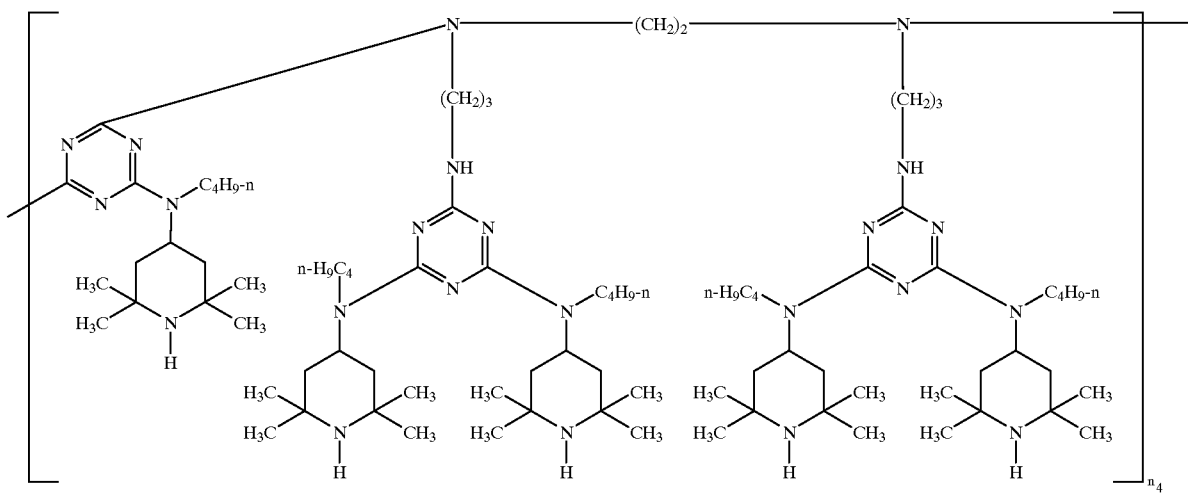

In the above formulae (VIII-1) to (VIII-3), $n_4$ is preferably 1 to 20, e.g. 2 to 20.

Preferred commercially available starting materials for the preparation of the compounds shown above under items a) to b), d) to g), i) to k) and m) to p) are ®TINUVIN 770, ®MARK LA 57, ®MARK LA 67, ®CHIMASSORB 905, ®CHIMASSORB 2020, ®CHIMASSORB 944, ®CYASORB UV 3346, ®DASTIB 1082, ®UVASIL 299, ®UVASORB HA 88, ®UVINUL 5050 H, ®LICHTSCHUTZSTOFF UV 31, ®LUCHEM HA-B 18, ®HOSTAVIN N 30, ®SUMISORB TM 61, ®MARK LA 68, ®UVINUL 4050 H, ®DIACETAM 5, ®UVINUL 4049 and ®FERRO AM 806.

Particularly preferred starting materials are the products disclosed in EP-A-850,938, especially the products disclosed therein in EXAMPLES 1 to 7, in particular EXAMPLE 1. EP-A-850,938 which is equivalent to U.S. patent application Ser. No. 08/994,977 filed on Dec. 19, 1997 is incorporated herein by reference.

Further particularly preferred starting materials are the products disclosed in EP-A-782,994, especially the products disclosed therein in EXAMPLES 1 to 12, in particular EXAMPLE 10. EP-A-782,994 which is equivalent to U.S. patent application Ser. No. 08/756,225 filed on Nov. 25, 1996 is also incorporated herein by reference.

In more detail, those products essentially known from EP-A-850,938, which correspond to the following formula (VI*) may be displayed as starting materials.

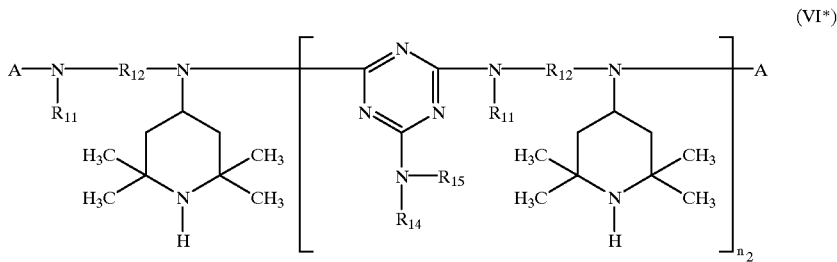

(VI*)

in which $n_2$ is a number from 2 to 14, in particular a number from 2 to 6, the radicals $R_{11}$, $R_{12}$, $R_{14}$ and $R_{15}$ independently of one another are as defined above, and the radicals A independently of one another are $C_1$–$C_{20}$acyl, ($C_1$–$C_8$alkoxy)carbonyl, ($C_5$–$C_{12}$cycloalkoxy)carbonyl, ($C_1$–$C_8$alkyl)aminocarbonyl, ($C_5$–$C_{12}$cycloalkyl) aminocarbonyl, ($C_7$–$C_9$phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —CH$_2$CN; in particular $C_1$–$C_{20}$acyl, especially $C_1$–$C_8$acyl.

Various examples of the above chemical meanings are listed further above.

Particularly preferred are those products of the formula (VI*) which have a narrow, well defined molecular weight distribution.

The polydispersity indicates the molecular-weight distribution of a polymeric compound. In the present application, the polydispersity is the ratio of weight-average ($\overline{Mw}$) and number-average ($\overline{Mn}$) molecular weights. A value of $\overline{Mw}/\overline{Mn}$ equal to 1 means that the compound is monodispers and has only one molecular weight and no molecular weight distribution. A narrow molecular weight distribution is characterized by a polydispersity close to 1.

Further, those products essentially known from EP-A-782,994, which correspond to the following formula (VI**) may be displayed as starting materials.

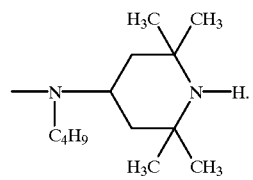

The starting materials of the formula (VI*) or (VI**) have preferably a polydispersity of 1 to 1.7, 1 to 1.65, 1 to 1.6, 1 to 1.55, 1 to 1.5, 1 to 1.45, 1.1 to 1.7, 1.1 to 1.65, 1.1 to 1.6, 1.1 to 1.55, 1.1 to 1.5, 1.1 to 1.45, 1.2 to 1.7, 1.2 to 1.65, 1.2 to 1.6, 1.2 to 1.55, 1.2 to 1.5, or 1.2 to 1.45. A polydispersity of 1.1 to 1.5 is particularly preferred.

GPC (Gel Permeation Chromatography) is used as an analytical procedure for separating molecules by their difference in size and to obtain molecular weight averages($\overline{Mw}$, $\overline{Mn}$) or information on the molecular weight distribution of polymers.

The technique is well known and described, for instance, in "Modern Size-Exclusion Liquid Chromatography" by W. W. Yan et al., edited by J.Wiley & Sons, N.Y., USA, 1979, pages 4–8, 249–283 and 315–340.

The GPC analyses of this application are carried out with a GPC chromatograph ®Perkin-Elmer LC 250 equipped with ®Perkin-Elmer RI detector LC 30 and with ®Perkin-Elmer oven LC 101.

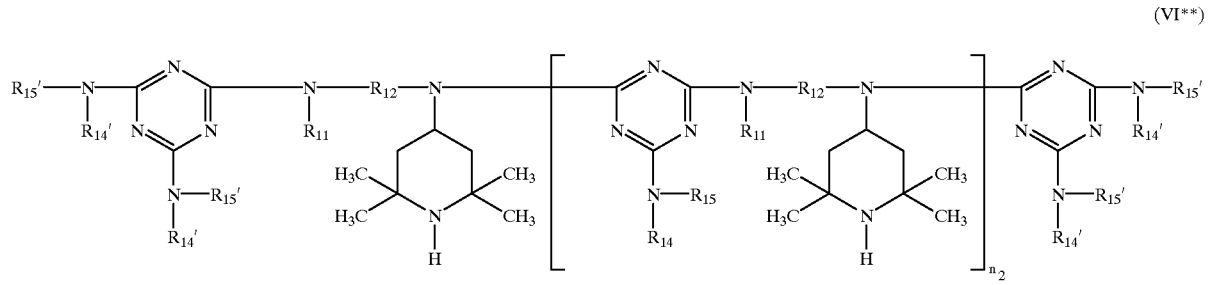

(VI**)

wherein $n_6$ is a number from 2 to 14, in particular a number from 2 to 6, $R_{11}$, $R_{12}$, $R_{14}$ and $R_{15}$ are as defined above, the radicals $R_{14}'$ independently of one another have one of the meanings given for $R_{14}$, the radicals $R_{15}'$ independently of one another have one of the meanings given for $R_{15}$, and the groups —N($R_{14}'$)($R_{15}'$) are identical or different.

According to a preferred embodiment, all groups —N($R_{14}'$)($R_{15}'$) are —N($C_1$–$C_{12}$alkyl)$_2$, in particular —N($C_4$H$_9$)$_2$ and all groups —N($R_{14}$)($R_{15}$) are All the analyses are carried out at 45° C. by using three columns PLGEL 3 $\mu$m Mixed E 300 mm length×7.5 mm i.d. (from Polymers Laboratories Ltd. Shropshire, U.K).

Tetrahydrofurane is used as eluant (flow 0.40 ml/min) and the samples are dissolved in tetrahydrofurane (2%) (% w/v).

EXAMPLE OF A PREPARATION PROCESS

The products described under a) to q) above can be prepared in analogy to known methods; for example by treating the abovementioned 2,2,6,6-tetramethylpiperidine derivative starting materials with an acylating agent such as an acyl chloride, an organic anhydride, a carboxylic acid or a carboxylic ester. A preferred acylating agent is an organic anhydride, in particular acetic anhydride. The molar ratio between the 2,2,6,6-tetramethyl-4-piperidyl groups in the starting material and the acylating agent depends on the desired degree of acylation in the final product. In order to acylate 50% of the original 2,2,6,6-tetramethyl-4-piperidyl groups in a compound, preferably 0.6 equivalents of acylating agent are used for one equivalent of 2,2,6,6-tetramethyl-4-piperidyl group to be acylated. The reaction is conveniently carried out in an inert organic solvent, for example toluene, xylene, benzene, n-hexane, an ether, tetrahydrofuran, chloroform or dichloromethane. Preferred solvents are xylene and toluene. The temperature is preferably 0° to 140° C., depending on the selected acylating agent. When the acylating agent is an organic anhydride, a temperature of 80° to 135° C. is preferred.

According to a particularly preferred embodiment of the invention, the acylation of the appropriate starting material is carried out using carboxylic acid anhydride, in particular acetic anhydride. Pursuant to this method, as a maximum, only 50% of the 2,2,6,6-tetramethyl-4-piperidyl >NH-groups can be acylated since the other 50% of these >NH-groups form a salt with the carboxylic acid liberated. After neutralizing with an appropriate base, e.g. NaOH, the corresponding free 2,2,6,6-tetramethyl-4-piperidyl groups are obtained from the salt. After isolation, the resultant product can be reacted in a second step with further carboxylic acid anhydride to give a product with a higher acylation degree, which in turn can again be reacted with carboxylic acid anhydride to give a product with an even higher acylation degree and so on. This procedure is illustrated in more detail e.g. in present EXAMPLES 1B and 2.

Therefore, a preferred embodiment of this invention also relates to a product containing 5 to 85% of a group (A-1-a) and/or (A-1-b)

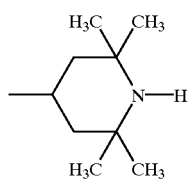

(A-1-a)

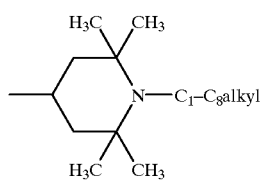

(A-1-b)

and 15 to 95% of a group (A-2-a),

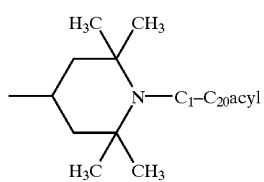

(A-2-a)

the total sum of the groups (A-1-a), (A-1-b) and (A-2-a) being 100%; obtainable (1) by reacting an appropriate starting material containing two or more groups of the formula

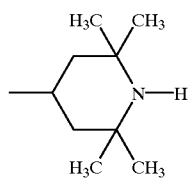

(A-1-a)

with $C_2$–$C_{40}$carboxylic acid anhydride in a molar ratio of up to 0.6 equivalent $C_2$–$C_{40}$carboxylic acid anhydride per 1 equivalent groups of the formula (A-1-a) to obtain an intermediate product which contains groups of the formula (A-2-a)

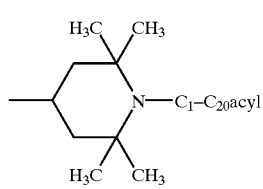

(A-2-a)

and groups of the formula (A-2-b)

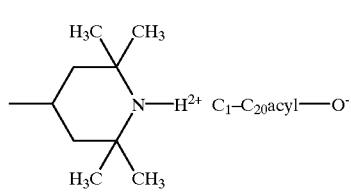

(A-2-b)

in a molar ratio of about 1:1,
reacting this intermediate with a base, e.g. an aqueous NaOH solution, to convert the groups of the formula (A-2-b) to groups of the formula (A-1-a), and isolating the resultant product; and (2) optionally repeating step (1) until the desired acylation degree is obtained.

In the above explanations, a preferred meaning of $C_1$–$C_{20}$acyl is $C_2$–$C_{20}$acyl or $C_2$–$C_{10}$acyl or $C_2$–$C_8$acyl and a preferred meaning of $C_2$–$C_{40}$carboxylic acid anhydride is $C_4$–$C_{40}$carboxylic acid anhydride or $C_4$–$C_{20}$carboxylic acid anhydride or $C_4$–$C_{16}$ carboxylic acid anhydride.

In general, the definition of the terminal groups which saturate the free valences in the products of the formulae (VI), (VII), (VIII-1), (VIII-2), (VIII-3), (IX), (XI), (XIII) and (XIX) depend on the processes used for their preparation. The terminal groups can also be modified after the preparation of the products.

In the products of the formula (VI), the end group attached to the diamino radical may be for example hydrogen, $C_1$–$C_{20}$acyl, ($C_1$–$C_8$alkoxy)carbonyl, ($C_5$–$C_{12}$cycloalkoxy)carbonyl, ($C_1$–$C_8$alkyl)aminocarbonyl, ($C_5$–$C_{12}$cycloalkyl)aminocarbonyl, ($C_7$–$C_9$phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; —$CH_2CN$ or a group of the formula

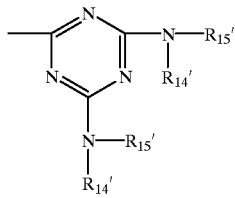

wherein the radicals $R_{14}'$ independently of one another have one of the meanings given for $R_{14}$, and the radicals $R_{15}'$ independently of one another have one of the meanings given for $R_{15}$ The end group attached to the triazinic ring may be for example halogen, e.g. Cl, or a group

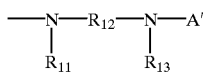

with A' being hydrogen, $C_1$–$C_{20}$acyl, ($C_1$–$C_8$alkoxy)carbonyl, ($C_5$–$C_{12}$cycloalkoxy)carbonyl, ($C_1$–$C_8$alkyl)aminocarbonyl, ($C_5$–$C_{12}$cycloalkyl)aminocarbonyl, ($C_7$–$C_9$phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; —CH$_2$CN or a group of the formula

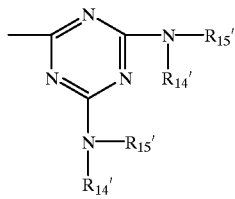

wherein the radicals $R_{14}'$ independently of one another have one of the meanings given for $R_{14}$, and the radicals $R_{15}'$ independently of one another have one of the meanings given for $R_{15}$.

When the end group attached to the triazinic ring is halogen, it is advantageous to replace it, for example, by —OH or an amino group when the reaction is complete. Examples of amino groups which may be mentioned are pyrrolidin-1-yl, morpholino, —NH$_2$, —N($C_1$–$C_8$alkyl)$_2$ and —NR($C_1$–$C_8$alkyl), in which R is hydrogen or a group of the formula (IV).

In the products of the formula (VII), the terminal group bonded to the silicon atom can, for example, be $(R_{16})_3$Si—O— and the end group bonded to the oxygen atom can, for example, be —Si($R_{16}$)$_3$.

The products of the formula (VII) can also exist as cyclic products if $n_3$ is a number from 3 to 10; in other words, the free valences depicted in the structural formula in that case form a direct bond.

In the intermediates of the formula (VIII-1), (VIII-2) and (VIII-3), the terminal group bonded to the triazine radical is, for example, Cl or a group

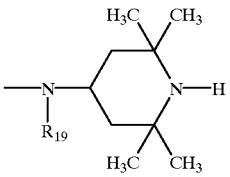

and the terminal group bonded to the amino radical is, for example, hydrogen or a group

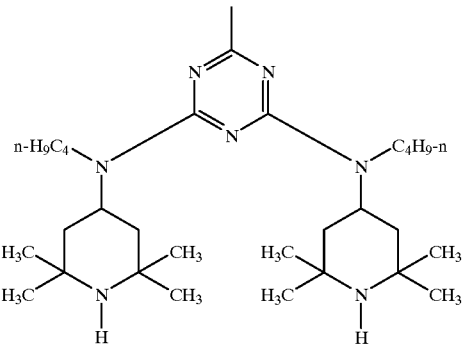

In the products of the formula (IX), the terminal group bonded to the 2,5-dioxopyrrolidine ring is, for example, hydrogen and the terminal group bonded to the radical —C($R_{27}$)($R_{28}$)— is, for example,

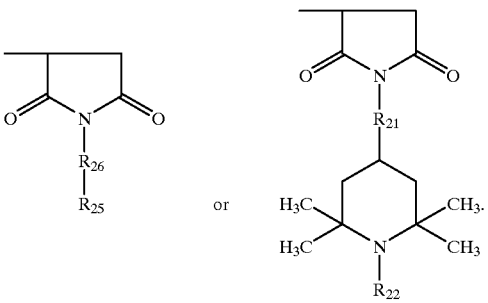

In the products of the formula (XI), the terminal group bonded to the dimethylene radical can, for example, be —OH and the terminal group bonded to the oxygen can, for example, be hydrogen. The terminal groups can also be polyether radicals.

In the products of the formula (XIII), the terminal group bonded to the carbonyl radical is, for example,

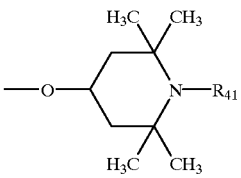

and the terminal group bonded to the oxygen radical is, for example,

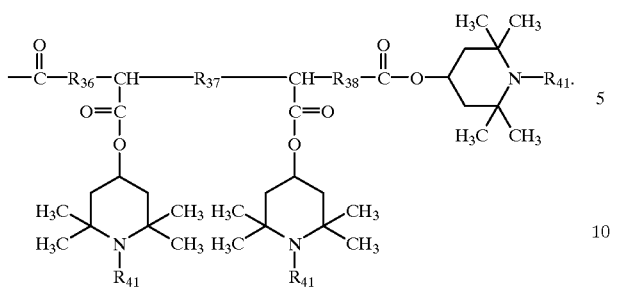

In the products of the formula (XIX), the terminal groups are for example hydrogen.

The products according to this invention are very effective in improving the light, heat and oxidation resistance of organic materials, especially synthetic polymers and copolymers.

Examples of organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EM and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly($\alpha$p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.
10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides, polyetherimids, polyesterimids, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/P PPO, PBT/PC/ABS or PBT/P ET/PC.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.

The invention thus also relates to a composition comprising an organic material susceptible to degradation induced by light, heat or oxidation and at least one product according to this invention.

The organic material is preferably a synthetic polymer, more particularly one selected from the aforementioned groups. Polyolefins, in particular polyethylene and polypropylene, are preferred. Polycarbonate such as listed in item 19 above, and blends of polycarbonate, such as listed in item 28 above are also preferred.

An organic material of interest is further a thermoplastic polyolefin, PP/EPDM, black pigmented PC-PBT blend, PVDC, PBT, PET, PVC or ASA/PVC.

Blends of polycarbonate with various styrenic polymers represent a growing family of materials for automotive usage. In particular blends of polycarbonate/acrylonitrile-butadiene-styrene and polycarbonate/acrylonitrile-styrene-acrylate are experiencing significant growth for automotive interior and exterior construction respectively. These materials offer an attractive combination of properties conferred by both components—improved notch sensitivity and high impact strength, lower melt viscosity and processing temperatures compared to pure polycarbonate. The light stabilization of pigmented polycarbonate/styrenic blends is a complex issue due to several factors, including the composition of the polymer blend components, and the selection and concentration of light and heat stable pigments. For instance, acrylonitrile-butadiene-styrene can be prepared by mass, emulsion, or hybrid technologies each of which carries over varying levels of emulsifiers, coagulants and stabilizers into the final polymer blend. The acrylonitrile-styrene-acrylate and acrylonitrile-butadiene-styrene terpolymers are multiphase materials of various compositions. The type of rubber and rubber content of such styrenic polymers can influence the gloss, color, impact and heat aging properties as the polymer (blend) undergoes weathering.

An impediment to even further growth of the pigmented or molded-in-color grades, is the difficulty in providing adequate light stabilization for a broad color palette. Copious information exists on the photodegradation and stabilization of the individual polycarbonate and styrenic polymers, yet limited information exists on the photodegradation of their blends. The light stabilization of polycarbonate blends is more complex than simply using the standard stabilizer systems for each polymer component in the blend.

Acceptable stabilizers for use in blends of polycarbonate should exhibit minimal detrimental interaction with the polymers during high temperature extrusion or molding. Melt rheology is a rapid method to assess the stability of a polymer in the melt state and thus to relate the interaction of any additives to changes in apparent melt viscosity and ultimately the molecular weight of the polymer. When melt rheology is conducted at a single, constant shear rate, a decrease in apparent melt viscosity over time can indicate that polymer degradation and molecular weight reduction is occurring.

The products according to this invention exhibit a significantly lower effect on polymer melt viscosity ratio than other sterically hindered amines. Further, they show only minimal interaction with the polymer blend in the molten state. The products according to this invention also improve color protection and retention of high impact strength, in particular in various pigmented polycarbonate/acrylonitrile-butadiene-styrene blends.

A further embodiment of this invention is a method for stabilizing an organic material against degradation induced by light, heat or oxidation, which comprises incorporating into said organic material at least one product according to this invention.

The products according to this invention can be used in various proportions depending on the nature of the material to be stabilized, on the end use and on the presence of other additives.

In general, it is appropriate to use, for example, 0.01 to 5% by weight of the products of this invention, relative to the weight of the material to be stabilized, preferably 0.05 to 2%, in particular 0.05 to 1%.

The products of this invention can be added, for example, to the polymeric materials before, during or after the polymerization or crosslinking of the said materials. Furthermore, they can be incorporated in the polymeric materials in the pure form or encapsulated in waxes, oils or polymers.

In general, the products of this invention can be incorporated in the polymeric materials by various processes, such as dry mixing in the form of powder, or wet mixing in the form of solutions or suspensions or also in the form of a masterbatch which contains the products of this invention in a concentration of 2.5 to 25% by weight; in such operations, the polymer can be used in the form of powder, granules, solutions, suspensions or in the form of latices.

The materials stabilized with the products of this invention can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, corrosion inhibitors and metal deactivators, can be added to the organic materials containing the products of this invention.

Particular examples of said conventional additives are:
1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(a-methylcyclohexyl)-4,6-dimethyl-phenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-di-methyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3, 5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3.5-di-tert-butyl-4-hydroxyphenyl) propionic acid e.g. N,N'-bis(3,5-di-tert-butyl-4-hydroxyphenylpropionyl)hexamethylenediamide, N,N'-bis (3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl- 2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1, 2,3,4-butane-tetracarboxylate, 1,1'-(1,2-ethanediyl)-bis(3,3, 5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2, 4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4, 6-trichloro-1,3,5-triazine as well as 4-butylamino-2,2,6,6-tetramethylpiperidine (CAS Reg. No. [136504-96-6]); N-(2, 2,6,6-tetramethyl-4-piperidyl)-n-dodecylsuccinimid, N-(1, 2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-

1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy) phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy}4,6-bis(2,4-dimethylphenyl)-1, 3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4, 6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-di-benz[d,g]-1,3,2-dioxaphosphocin, 6-fluoro-2,4,8,10-tetra-tert-butyl-12-methyl-dibenz[d,g]-1, 3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3', 5,5'-tetra-tert-butyl-1,1'-biphenyl-2,2'-diyl)phosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters β-thiodipropionic acid, for example the lauryl, stearyl, myristyl or tridecyl esters, mercaptobenzimidazole or the zinc salt of 2-mercaptobenzimidazole, zinc dibutyidithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338, 244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3, 5-dimethylphenyl)-5,7-di-tert-butyl-benzofuran-2-one, 3-(3, 5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The weight ratio of the compounds of this invention to the conventional additives may be 1:0.5 to 1:5.

The products according to this invention are preferably used in combination with a pigment and/or an UV absorber.

The products of the invention can also be used as stabilizers, especially as light stabilizers, for almost all materials known in the art of photographic reproduction and other reproduction techniques as e.g. described in Research Disclosure 1990, 31429 (pages 474 to 480).

The invention is illustrated in more detail by the following Examples. All percentages are by weight, unless otherwise indicated.

In the structural formulae of the following examples, $n_2'$, $n_3'$ and $n_7'$ indicate that there are repetitive units in the molecules and the products obtained are not uniform.

In the following examples, the acylation degree is determined as described below.

DETERMINATION OF THE ACYLATION DEGREE

The analytical determinations are carried out by titration, in a non aqueous environment, using perchloric acid in isopropanol as reagent and a mixture (1:1) of chloroform and acetonitrile as solvent.

Two different measurements are needed to get the result: in the first one, the starting material (oligomer carrying only free NH groups in the piperidyl moieties) is titrated, obtaining a number (A) index of the amount of free NH groups in the compound; the second titration is performed on the final acylated product and gives the number (B) index of the residual free NH groups after the acylation reaction.

The "% acylation degree" is calculated as (100−B×100/A).

EXAMPLE 1

A) Preparation of the Intermediate of the Formula

After washing with water, the organic phase is concentrated under vacuum at 60°–70° C./10 mbar, being 125 ml of xylene recovered.

69 g (0.175 moles) of N,N'-bis[2,2,6,6-tetramethyl-4-piperidinyl]-1,6-hexanediamine are added and the mixture is heated to 150° C. for 2 hours, cooled again and 7g (0.175 moles) of ground sodium hydroxide are added.

The mixture is heated to 140° C. for further 4 hours, being the residual water of reaction eliminated off azeotropically, and for further 4 hours at 160° C.

After cooling to 60° C., the mixture is diluted with 130 ml of xylene, filtered and washed three times with 50 ml of ethylene glycol.

After concentrating under vacuum at 60° C./10 mbar, 7.5 g (0.073 moles) of acetic anhydride are added. After ½ hour

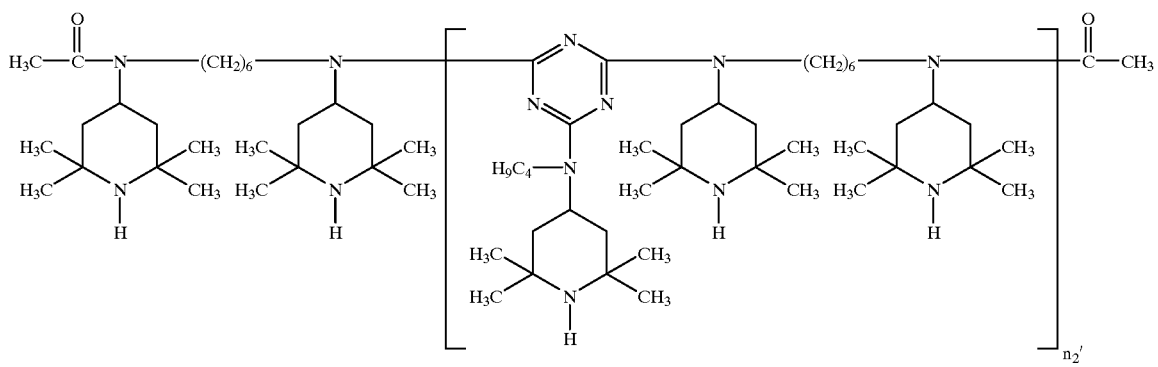

A solution of 37.1 g (0.175 moles) of N-(2,2,6,6-tetramethyl-4-piperidinyl)-n-butylamine in 30 ml of water is slowly added at 0° C. to a solution of 32.2 g (0.175 moles) of cyanuric chloride in 250 ml of xylene, keeping the temperature during the addition and for further 1 hour.

After 2 hours at room temperature, the mixture is cooled to 0° C. and an aqueous solution of 7.3 g (0.18 moles) of sodium hydroxide in 25 ml of water is added. After ½ hour at 0° C. and further 2 hours at room temperature, the aqueous solution is separated off and 34.6 g (0.087 moles) of N,N'-bis[2,2,6,6-tetramethyl-4-piperidinyl]-1,6-hexanediamine are added.

The mixture is heated to 50° C. for 1 hour and 24.2 g (0.175 moles) of ground potassium carbonate are added and heated to 60° C. for 4 hours.

at room temperature, the mixture is heated to 130° C. for 5 hours. After cooling to room temperature, 20.2 g (0.146 moles) of ground potassium carbonate are added and the mixture is heated to 130° C. for 2 hours.

Then, the mixture is cooled to 50° C., filtered and concentrated under vacuum at 140° C./1 mbar.

A solid with a melting range of 128°–134° C. is obtained after drying.

$\overline{Mn}$ (by GPC)=2712 g/mole $\overline{Mw/Mn}$=1.41

B) Preparation of the Product of the Formula

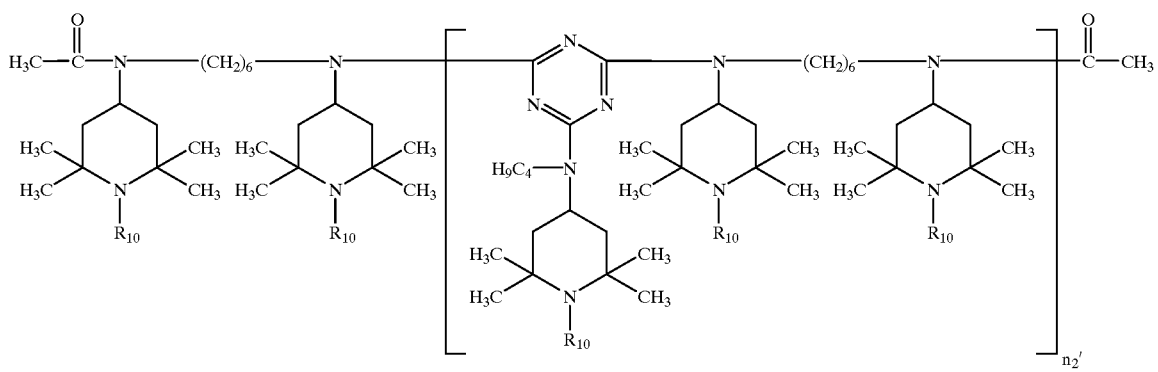

wherein 45 to 55% of the radicals $R_{10}$ are acetyl and the remaining radicals $R_{10}$ are hydrogen.

150 g (1.47 mol) of acetic anhydride are added to a solution of 290 g of the intermediate described under A), dissolved in 400 ml of toluene. The solution is heated to reflux for eight hours. Then, the solution is cooled to 60° C. and 13.1 g of NaOH in 500 ml of water are slowly added. The mixture is left under stirring for additional 5 hours. After cooling to room temperature, the organic layer is separated, washed three times with 100 ml of water, dried over sodium sulfate and concentrated under vacuum. The desired product is obtained as a white powder with a melting range of 127°–137° C.

$\overline{Mn}$ (by GPC)=2500 g/mole
$\overline{Mw}/\overline{Mn}$=1.33

EXAMPLE 2
Preparation of the Product of the Formula

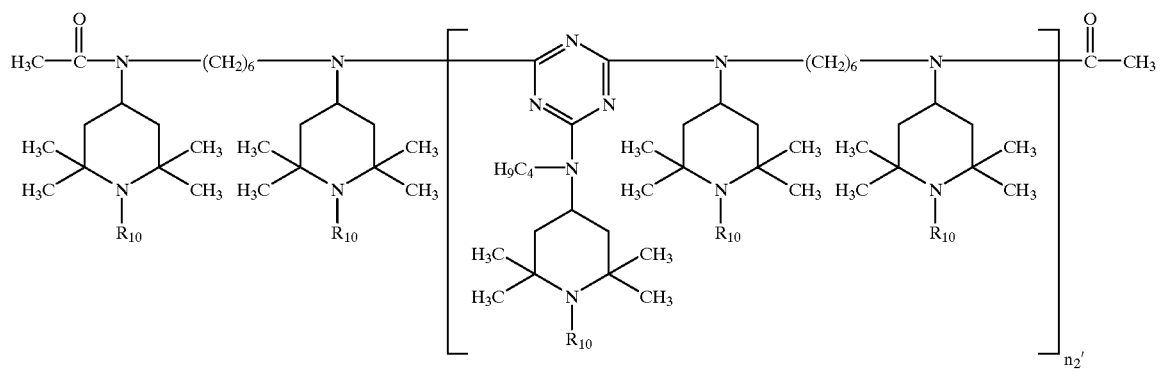

wherein 70 to 80% of the radicals $R_{10}$ are acetyl and the remaining radicals $R_{10}$ are hydrogen.

40 g of acetic anhydride are added to a solution of 145 g of the intermediate of EXAMPLE 1B) in 200 ml of toluene. The solution is heated to reflux for 6 hours. Then, the solution is cooled to room temperature and a solution of 48 g of NaOH in 200 ml of water is added. The mixture is heated to 70° C. and allowed to react for additional 6 hours.

The organic phase is separated off, washed three times with 100 ml of water, dried over sodium sulfate and evaporated under vacuum. The desired product is obtained as a white powder with a melting range of 132°–138° C.

$\overline{Mn}$ (by GPC)=2650 g/mole
$\overline{Mw}/\overline{Mn}$=1.29

EXAMPLE 3
Preparation of the Compound of the Formula

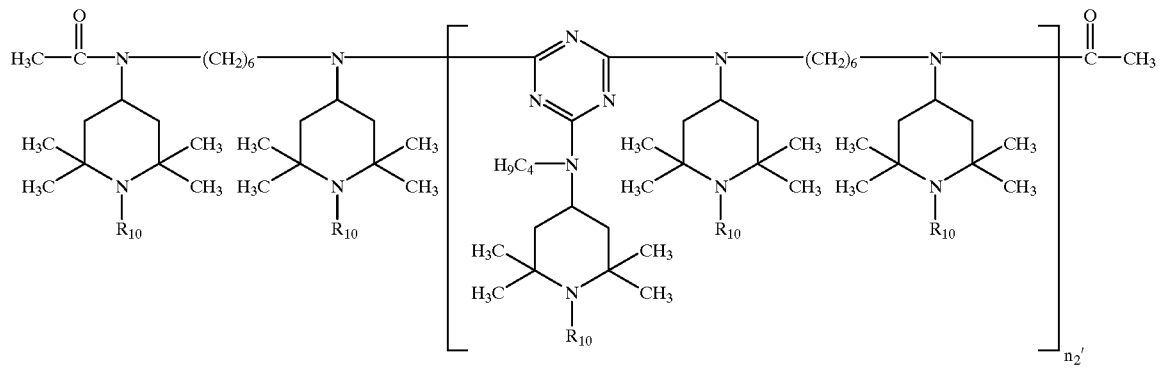

wherein 55–65% of the radicals $R_{10}$ are acetyl and the remaining radicals $R_{10}$ are methyl.

70 g of the compound of EXAMPLE 1B are dissolved in an aqueous solution of 15.5 g (0.34 mol) of formic acid in 100 ml of water. Then, 15 g (0.5 mol) of paraformaldehyde are added and the aqueous solution is heated under reflux for 16 hours. After cooling to room temperature, 100 ml of xylene are added. After stirring for 2 hours, 15.5 g (0.39 mol) of NaOH in 100 ml of water are added. Subsequently, the organic phase is separated off, washed twice with water and dried over sodium sulfate. After filtration, the organic phase is evaporated under vacuum. The desired product is obtained as a white powder with a melting range of 134°–139° C.

EXAMPLE 4

Preparation of the Compound of the Formula

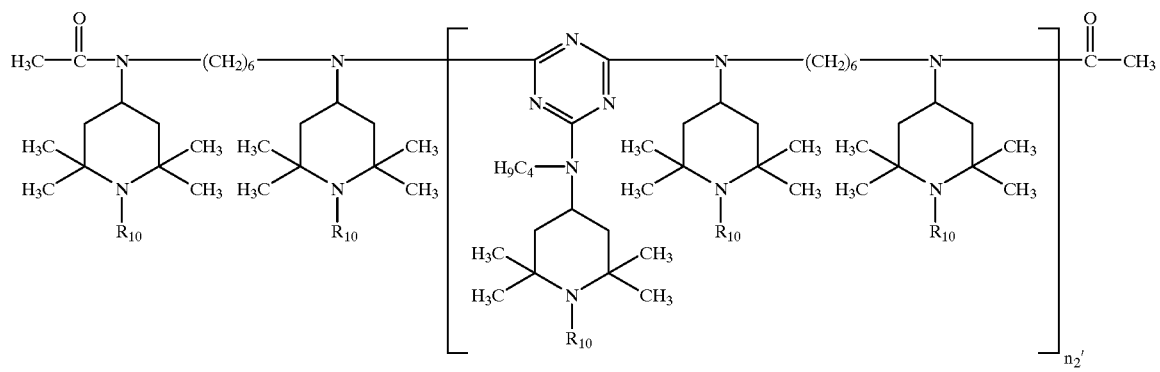

wherein 15–25% of the radicals $R_{10}$ are acetyl and the remaining radicals $R_{10}$ are hydrogen.

Following the procedure reported in EXAMPLE 1B and using the appropriate amount of reagents (6.5 g of acetic anhydride for 51.5 g of the compound of EXAMPLE 1A) the desired compound is obtained as a white powder with a melting range of 125°–133° C.

EXAMPLE 5

Preparation of the Compound of the Formula

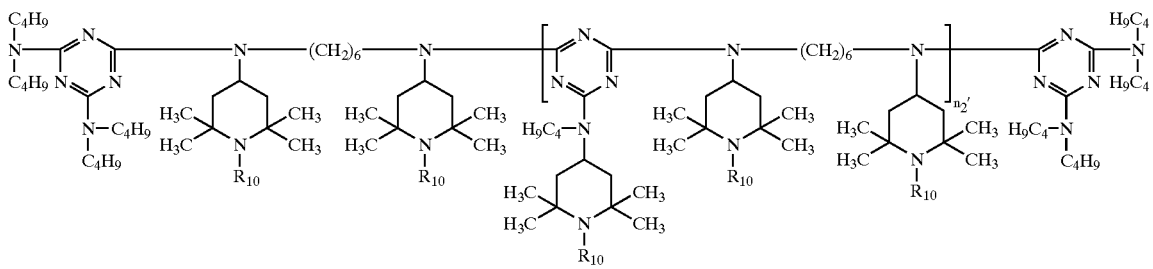

wherein 55–65% of the radicals $R_{10}$ are acetyl and the remaining radicals $R_{10}$ are hydrogen.

Following the procedure reported in EXAMPLE 1B, using the commercial product ®CHIMASSORB 2020 as starting material and the right amount of reagents (155 g of acetic anhydride for 300 g of ®CHIMASSORB 2020) the desired compound is obtained as a white powder with a melting range of 126°–135 ° C.

EXAMPLE 6
Preparation of the Compound of the Formula

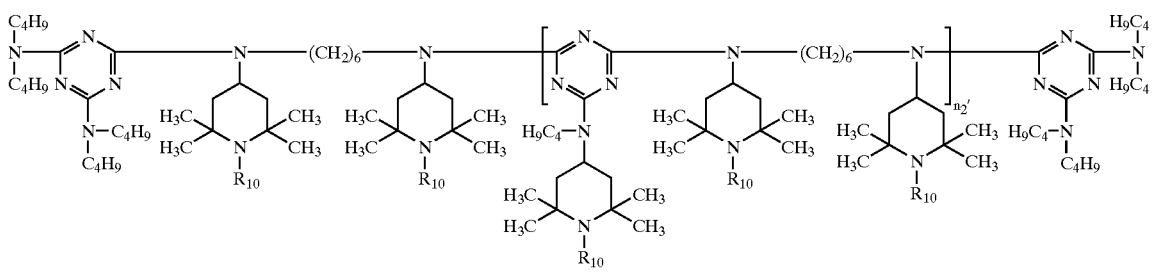

wherein 75–85% of the radicals $R_{10}$ are acetyl and the remaining radicals $R_{10}$ are hydrogen.

Following the procedure reported in EXAMPLE 1B, using the product of EXAMPLE 5 as starting material and the right amount of reagents (77.8 g of acetic anhydride for 150 g of the product of EXAMPLE 5) the desired compound is obtained as a white powder with a melting range of 131°–138° C.

EXAMPLE 7
A) Preparation of the Intermediate of the Formula:

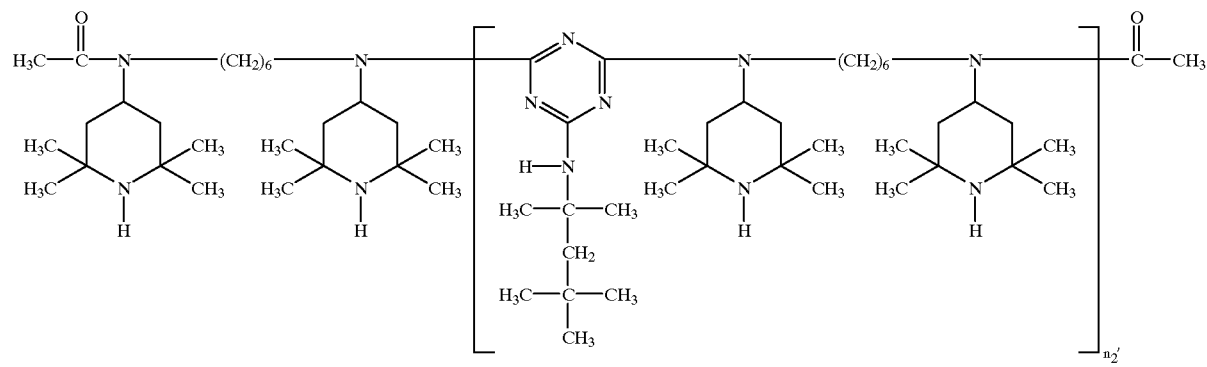

Following the procedure reported in EXAMPLE 1A, using the commercial product ®CHIMASSORB 944 as starting material and the right amount of reagents (50 g of acetic anhydride for 400 g of ®CHIMASSORB 944) the desired intermediate is obtained with a melting range of 120°–125° C.

B) Preparation of the Compound of the Formula:

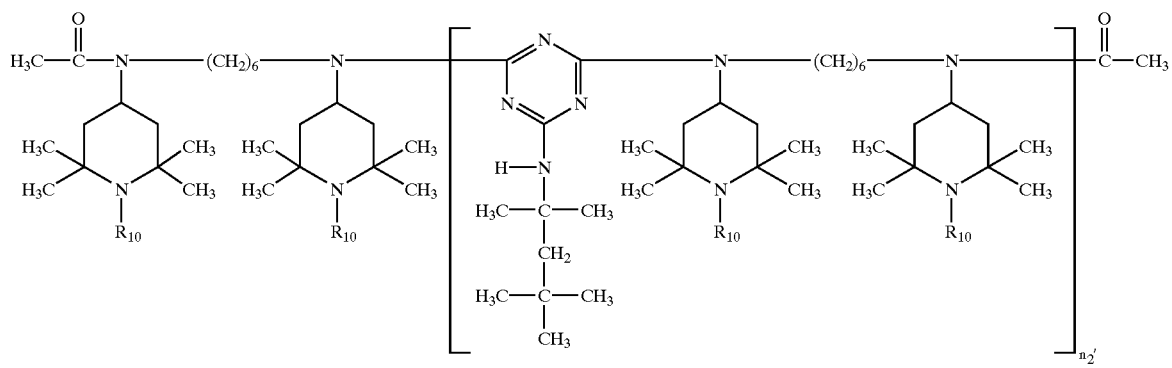

wherein 45–55% of the radicals $R_{10}$ are acetyl and the remaining radicals $R_{10}$ are hydrogen.

Following the procedure reported in EXAMPLE 1B, using the intermediate of EXAMPLE 7A as starting material and the right amount of reagents (175 g of acetic anhydride for 340 g of the compound of EXAMPLE 7A) the desired compound is obtained as a white powder with a melting range of 121°–127° C.

EXAMPLE 8

Preparation of the Compound of the Formula:

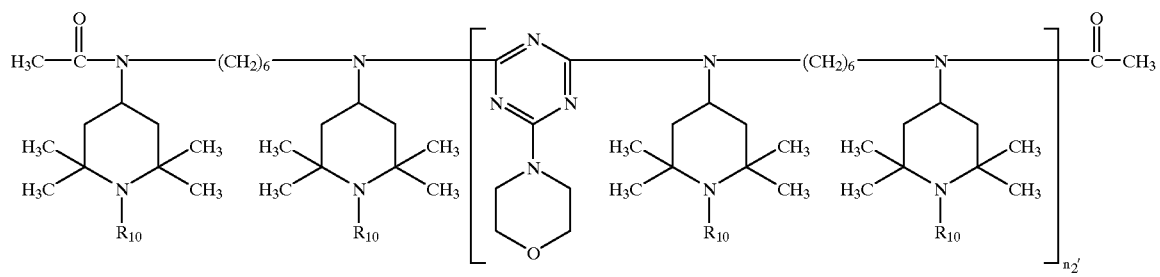

wherein 50–60% of the radicals $R_{10}$ are acetyl and the remaining radicals $R_{10}$ are hydrogen.

Following the procedure reported in EXAMPLE 1B, using the commercial product ®CYASORB UV 3346 as starting material and the right amount of reagents (99.4 g of acetic anhydride for 160 g of ®CYASORB UV 3346) the desired compound is obtained as a white powder with a melting range of 122°–134° C.

EXAMPLE 9

Preparation of the Compound of the Formula

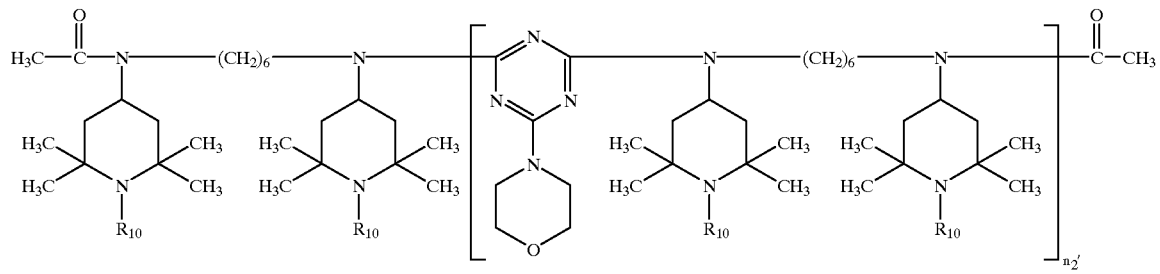

wherein 70–80% of the radicals $R_{10}$ are acetyl and the remaining radicals $R_{10}$ are hydrogen.

Following the procedure reported in EXAMPLE 1B, using the compound of EXAMPLE 8 as starting material and the right amount of reagents (41.5 g of acetic anhydride for 80 g of the compound of EXAMPLE 8) the desired compound is obtained as a yellow powder with a melting range of 135°–143° C.

EXAMPLE 10

Preparation of the Compound of the Formula

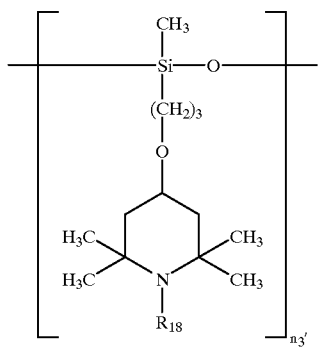

wherein 70–80% of the radicals $R_{18}$ are acetyl and the remaining radicals $R_{18}$ are hydrogen.

Following the procedure reported in EXAMPLE 1B. using the commercial product ®UVASIL 299 as starting material and the right amount of reagents (21.6 g of acetic anhydride for 38 g of ®UVASIL 299) the desired compound is obtained as an orange oil.

EXAMPLE 11

Following the procedure reported in EXAMPLE 1B, using the commercial product ®UVASORB HA 88 which contains groups of the formula (A-1-a)

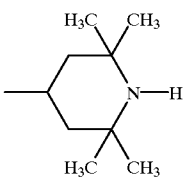

(A-1-a)

as starting material and the right amount of reagents (80 g of acetic anhydride for 62 g of ®UVASORB HA 88) the desired compound wherein 55–65% of the groups (A-1-a) are acetylated is obtained as a yellow powder with a melting range of 126°–131° C.

EXAMPLE 12

Preparation of the Compound of the Formula

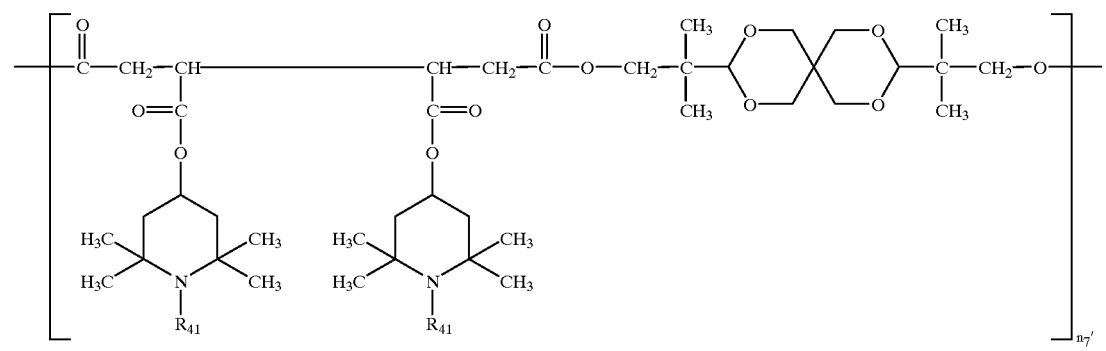

wherein 75–85% of the radicals $R_{41}$ are acetyl and the remaining radicals $R_{41}$ are hydrogen.

Following the procedure reported in EXAMPLE 1B and using the commercial product ®MARK LA 68 as starting material and the right amount of reagents (30 g of acetic anhydride for 40 g of MARK LA 68) the desired compound is obtained as a pale brown powder with a melting range of 92°–97° C.

EXAMPLE 13
Preparation of the Product Mixture of the Formula

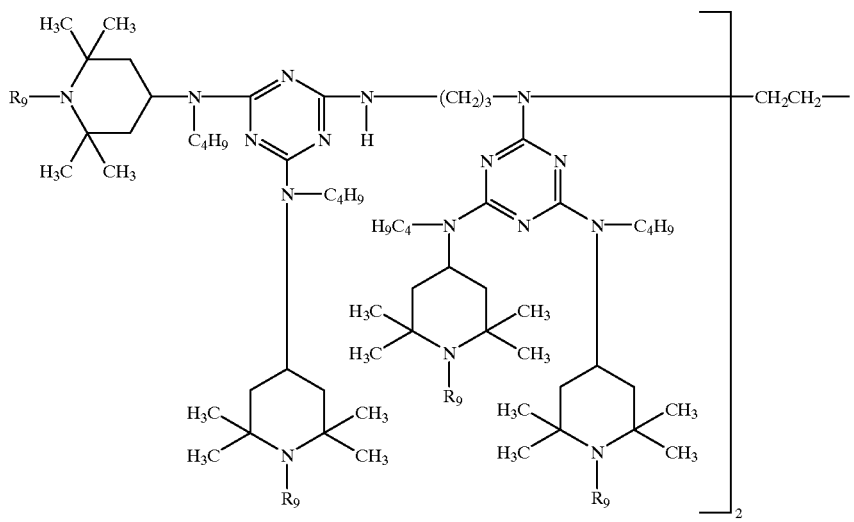

wherein 55–65% of the radicals $R_9$ are acetyl and the remaining radicals $R_9$ are hydrogen.

Following the procedure reported in EXAMPLE 1B. using the commercial product ®CHIMASSORB 905 as starting material and the right amount of reagents (207 g of acetic anhydride for 350 g of ®CHIMASSORB 905) the desired product is obtained as a yellow powder with a melting range of 122°–126° C.

EXAMPLE 14
Preparation of the Product Mixture of the Formula

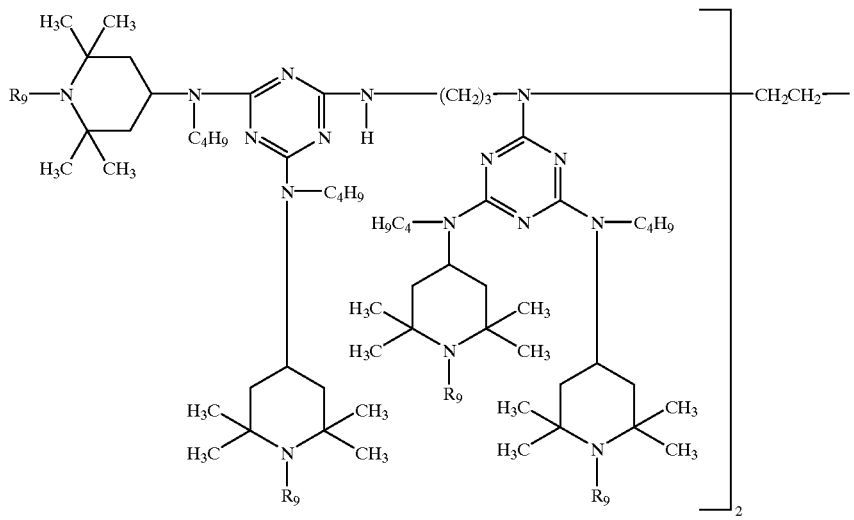

wherein 55–65% of the radicals $R_9$ are acetyl and the remaining radicals $R_9$ are methyl.

Following the procedure described in EXAMPLE 3 and using the compound of EXAMPLE 13 as starting material the desired product is obtained as a yellow powder with a melting range of 132°–136° C.

EXAMPLE 15
Preparation of the Product Mixture of the Formula

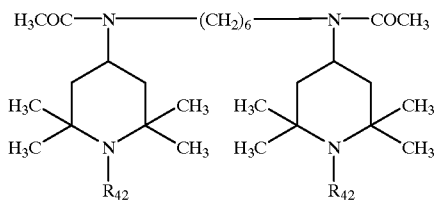

wherein 55–65% of the radicals $R_{42}$ are acetyl and the remaining radicals $R_{42}$ are hydrogen.

Following the procedure reported in EXAMPLE 1B and using N,N'-bis{2,2,6,6-tetramethypiperidin-4-yl}hexane-1,6-diamine as starting material and the right amount of reagents (112 g of acetic anhydride for 42 g of N,N'-bis{2,2,6,6-tetramethylpiperidin-4-yl}hexane-1,6-diamine) the desired product is obtained as a white powder with a melting range of 134°–138° C.

EXAMPLE 16
Preparation of the Product Mixture of the Formula

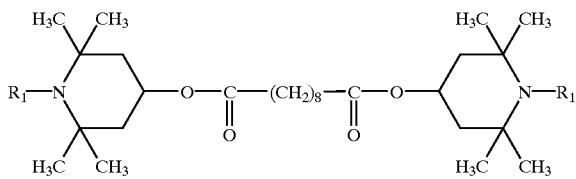

wherein 75–85% of the radicals $R_1$ are acetyl and the remaining radicals $R_1$ are hydrogen.

Following the procedure reported in EXAMPLE 1B and using ®TINUVIN 770 as starting material and the right amount of reagents (63 g of acetic anhydride for 100 g of ®TINUVIN 770) the desired product is obtained as a pale yellow oil.

$^1$H NMR (300 MHz, CDCl$_3$) ppm: 5.1 (m, 2H); 2.2 (m, 4H); 2.1 (s, 5H); 1.9 (m, 4H); 1.6 (m, 4H); 1.4 (s, 12H); 1.3 (s, 12H); 1.2 (m, 8H); 1.0 (t, 4H).

EXAMPLE I-1
Stabilization of a Gray Pigmented Polycarbonate/acrylonitrile-butadiene-styrene (PC/ABS) Blend.

A commercial PC/ABS blend (®Cycoloy MC 8002) pigmented with 1% by weight of ®Gray 9779 from Uniform Color Company is stabilized by addition of 1% by weight of 2-(2'-hydroxy-3',5'-bis(1",1"-dimethylbenzyl)phenyl) benzotriazole and 0.5% by weight of the compound indicated in Table I-1. A sample containing only the 1% by weight of the benzotriazole stabilizer and an unstabilized sample—both containing 1% by weight of gray pigment—serve as comparison.

Izod bars (2.5"L×0.5"W×0.125"W) are prepared by injection molding on a ®BOY 30 machine, barrel temperature 246°–268° C., die temperature 268° C. Accelerated weathering is performed using an ®Atlas Ci65A Weather-O-meter (XAW), operating in "Dry XAW" mode (ASTM G26-90, method C). After regular intervals, the color change ΔE according to DIN 6174 is determined. The results are listed in Table I-1.

TABLE I-1

| Irradiation time:<br>Stabilizer | 249.8 hours<br>ΔE | 750 hours<br>ΔE |
|---|---|---|
| None | 2.4 | 7.8 |
| Benzotriazole stabilizer*) | 1.3 | 5.5 |
| Compound of EXAMPLE 1B | 0.4 | 2.4 |
| Compound of EXAMPLE 2 | 0.5 | 3.1 |

*)2-(2'-hydroxy-3',5'-bis(1",1"-dimethylbenzyl)phenyl)benzotriazole

The PC/ABS samples stabilized according to this invention show an excellent color stability.

EXAMPLE I-2
Stabilization of a Blue Pigmented Polycarbonate/acrylonitrile-butadiene-styrene (PC/ABS) Blend.

Samples are prepared from a commercial PC/ABS blend (®Cycoloy MC 8002) as described in EXAMPLE I-1 except that 1% by weight of ®Blue 120A from ®Uniform Color Company is used as pigment and is stabilized by addition of 0.75% by weight of 2-(2'-hydroxy-3',5'-bis(1",1"-dimethylbenzyl)phenyl)benzotriazole and 0.5% by weight of the compound indicated in Table I-2. A sample containing only the 0.75% by weight of the benzotriazole stabilizer and an unstabilized sample—both containing 1% by weight of blue pigment—serve as comparison. Weathering and assessment is carried out as described in EXAMPLE I-1.

The results are shown in Table I-2.

TABLE 1-2

| Irradiation time:<br>Stabilizer | 249.6 hours<br>ΔE | 749.3 hours<br>ΔE | 999.8 hours<br>ΔE |
|---|---|---|---|
| None | 3.6 | 9.7 | 12.4 |
| Benzotriazole stabilizer*) | 2.6 | 9.7 | 12.9 |
| Compound of EXAMPLE 1B | 0.5 | 3.8 | 6.1 |

*)2-(2'-hydroxy-3',5'-bis(1",1"-dimethylbenzyl)phenyl)benzotriazole

The PC/ABS samples stabilized according to this invention show an excellent color stability, particularly at prolonged exposure intervals.

EXAMPLE I-3
Stabilization of a White Pigmented Polycarbonate/acrylonitrile-butadiene-styrene (PC/ABS) Blend.

A commercially available white pigmented (TiO$_2$) PC/ABS blend (®Cycoloy MC 8002-822; Polymerland Inc.) is stabilized by addition of 1% by weight of tris{2,4-di-tert-butylphenyl}phosphite, 0.75% by weight of 2-(2'-hydroxy-3',5'-bis(1",1"-dimethylbenzyl)phenyl)benzotriazole and 0.5% by weight of the compound indicated in Table I-3.

The extrusion is carried out on a ®Leistritz 18 mm corotating, intermeshing twin screw extruder (general temperature profile (throat to die in ° C.): 220, 240, 245, 245, 245, 245, 245; extrudate temperature: 256–258° C.). The polymer is predried in vacuo to <50 ppm moisture.

Izod bars (2.5"L×0.5"W×0.125"W) are prepared by injection molding on a ®BOY 50 machine (set temperatures= 268° C., 268° C., 271° C.; nozzle=271–279° C.; injection pressure=49.2 at; holding pressure=49.2 at; back pressure= 8.44 at).

Accelerated weathering is performed using an ®Atlas Ci-65 Weather-O-meter (Xenon-Arc Weather-O-meter)

operated per ASTM G26-90 method C (black panel temperature: 63° C.; irradiance: 0.35 W/m²; inner and outer filters: borosilicate).

The results are listed in Table I-3.

TABLE I-3

| Irradiation time:<br>Stabilizer | 249.8 hours<br>ΔE | 750 hours<br>ΔE |
| --- | --- | --- |
| None | 3.8 | 12.6 |
| Compound of EXAMPLE 1B | 1.1 | 6.6 |
| Compound of EXAMPLE 3 | 1.0 | 6.1 |
| Compound of EXAMPLE 4 | 1.1 | 6.5 |
| Compound of EXAMPLE 5 | 1.1 | 6.8 |
| Compound of EXAMPLE 8 | 1.3 | 6.9 |
| Compound of EXAMPLE 10 | 1.1 | 6.6 |
| Compound of EXAMPLE 11 | 1.1 | 6.4 |
| Compound of EXAMPLE 13 | 1.0 | 6.6 |
| Compound of EXAMPLE 14 | 1.0 | 6.4 |
| Compound of EXAMPLE 16 | 1.0 | 5.7 |

The PC/ABS samples stabilized according to this invention show an excellent color stability.

EXAMPLE II-1
Stabilization of Polyethylene Films, Treated or Untreated with Pesticides.

The stabilizers indicated in Table II-1 are mixed with low density polyethylene (LDPE) pellets (®Riblene FF 29 supplied by ®ENICHEM, Milano, Italy; melt flow index at 190° C. and 2.16 kg: 0.62 g/10 min) in a turbo mixer.

The mixture is extruded at a maximum temperature of 200° C. in a ®Berstorff single-screw extruder and the granules so obtained are compression molded in a ®Pasadena press for 3 min at 170° C. Films of about 150 μm thickness containing 0.3% of the stabilizer are obtained.

Pressmolded films for pesticide treatment are kept inside a dryer for 24 hours at 30° C., in presence of the vapors emitted by 2 liter of an aqueous solution containing 50% of ®VAPAM (®Baslini S.p.A., Treviglio, Bergamo, Italy), which, in turn, is an aqueous solution of 382 g per liter of metam-sodium having the formula $CH_3-NH-CS-SNa$.

Non-treated films are mounted in metal frames while treated films are put into quartz tubes. Frames and tubes are exposed in an ®Atlas Ci 65 Xenon Arc Weather-O-meter at 63° C. black panel temperature, continuos dry cycle, according to ASTM G 26-96. During the exposure, the performance is periodically evaluated measuring the carbonyl increment by means of a Fourier Transform Infrared (FT-IR) Spectrophotometer. The results are summarized in Table II-1.

TABLE II-1

| Stabilizer | Pesticide treated;<br>time (hours)<br>to carbonyl<br>increment = 0.2 | Non treated;<br>time (hours)<br>to carbonyl<br>increment = 0.1 |
| --- | --- | --- |
| Without | <250 | <500 |
| 0.3% of the compound of EXAMPLE 1B | 270 | 3190 |
| 0.3% of the compound of EXAMPLE 2 | 295 | 4250 |

(High values indicate a good stabilization.)

EXAMPLE II-2
Stabilization of Polypropylene Fibres.

0.25% of the stabilizer listed in Table II-2 is mixed with polypropylene powder (®Moplen FL F20 supplied by ®Montell, Ferrara, Italy; melt flow index at 230° C. and 2.16 Kg: 12.2 g/min) in a turbo mixer together with 0.1% of tris(2,4-di-t-butylphenyl) phosphite, 0.1% of calcium monoethyl 3,5-di-t-butyl-4-hydroxybenzyl-phosphonate, 0.1% of calcium stearate and 0.25% of titanium dioxide ("%" means "% by weight relative to the weight of the polypropylene").

The mixture is extruded at a maximum temperature of 230° C. in a ®Berstorff single-screw extruder and the granules so obtained are converted into multifilaments at a maximum temperature of 260° C. by fiber spinning in a ®Leonard apparatus (120/12 deniers). Multifilaments for tentering are exposed in a forced circulating air oven for 20 min at 120° C. Non treated and tentered multifilaments are exposed in an ®Atlas Ci 65 Xenon Arc Weather-O-meter at 63° C. black panel temperature, continuos dry cycle, according to ASTM G 26-96. During the exposure, the performance is periodically evaluated measuring the retained tensile strength by an Instron dynamometer. The results are indicated in Table II-2.

TABLE II-2

| | % retained tensile strength | |
| --- | --- | --- |
| Stabilizer | tel quel | tentered |
| Without | 50 after 200 hours | 50 after 150 hours |
| Compound of EXAMPLE 1B | 72 after 1450 hours | 72 after 1450 hours |

(High values indicate a good stabilization.)

EXAMPLE II-3
Stabilization of Polypropylene Multifilaments and Polypropylene Plaques.

Polypropylene multifilaments are prepared as described in EXAMPLE II-2.

Injection molded plaques of 1 mm thickness are prepared, starting by adding to polypropylene powder (®Moplen S SF supplied by ®Montell, Ferrara, Italy; melt flow index at 230° C. and 2.16 Kg: 2.0 g/min), 0.1% of the stabilizer listed in Table II-3, 0.1% of tris(2,4-tert-butylphenyl) phosphite, 0.5% of octadecyl-3-(3,5-di-tert-butyl-4-hydroxyphenyl) propionate and 0.1% of calcium stearate, and mixing the components in a turbo mixer ("%" means "% by weight relative to the weight of the polypropylene"). The mixture is extruded at a maximum temperature of 230° C. in a ®Berstorff single-screw extruder and the granules so obtained are converted into plaques 1 mm thick by injection molding in a ®Negri-Bossi press at a maximum temperature of 220° C.

The multifilaments and the plaques so obtained are exposed in a forced circulating air oven at 120° C. and 135° C., respectively.

Evaluations are periodically made until breakage occurs. For multifilaments this event corresponds to falling down of a weight that had been hung to each fiber formulation; for plaques the evaluation is made by bending it with a specific device.

The results are summarized in Table II-3.

TABLE II-3

| Stabilizer | Hours to breakage of multifilaments at 120° C. | Hours to breakage of plaques at 135° C. |
| --- | --- | --- |
| without | 120 | 790 |
| Compound of EXAMPLE 1B | 1150 | 1320 |

(High values indicate a good stabilization.)

What is claimed is:

1. A product containing
5 to 85% of a group (A-1-a) and/or (A-1-b)

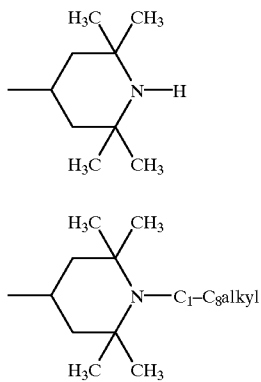

and 15 to 95% of a group (A-2),

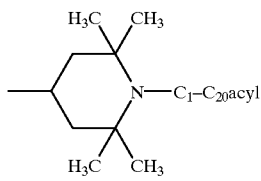

the total sum of the groups (A-1-a), (A-1-b) and (A-2) being 100%.

2. A product according to claim 1, which corresponds to the formula (I) as defined under a), the formula (II) as defined under b), the formula (V) as defined under c), the formula (VI) as defined under d), the formula (VII) as defined under e), a reaction product as defined under f), or which corresponds to the formula (IX) as defined under g), the formula (X) as defined under h), the formula (XI) as defined under i), the formula (XII) as defined under j), the formula (XIII) as defined under k), the formula (XIV) as defined under l), the formula (XVI) as defined under m), the formula (XVII) as defined under n), the formula (XVIII) as defined under o) or the formula (XIX) as defined under p);

a) a product mixture of the formula

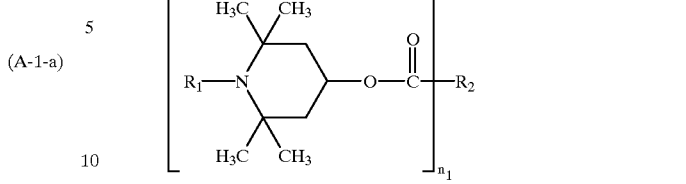

in which
the radicals $R_1$ independently of one another are hydrogen, $C_1$–$C_8$alkyl or $C_1$–$C_{20}$acyl with 5 to 85% of the total sum of the radicals $R_1$ independently of one another being hydrogen or $C_1$–$C_8$alkyl and the remaining radicals $R_1$ being $C_1$–$C_{20}$acyl;
$n_1$ is 2 or 4,
if $n_1$ is 2, $R_2$ is $C_1$–$C_{14}$alkylene or bis{($C_1$–$C_{20}$alkyl)oxycarbonyl}$C_4$–$C_{10}$alkanetetrayl, and
if $n_1$ is 4, $R_2$ is $C_4$–$C_{10}$alkanetetrayl;

b) a product mixture of the formula

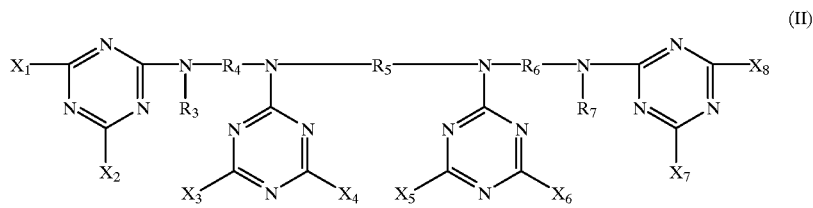

in which
$R_3$ and $R_7$ independently of one another are hydrogen or $C_1$–$C_{12}$alkyl,
$R_4$, $R_5$ and $R_6$ independently of one another are $C_2$–$C_{10}$alkylene, and
$X_1$, $X_2$, $X_3$, $X_4$, $X_5$, $X_6$, $X_7$ and $X_8$ independently of one another are a group of the formula (III),

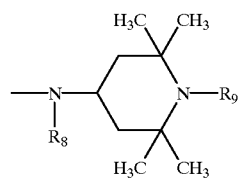

in which $R_8$ is hydrogen, $C_1$–$C_{12}$alkyl, $C_5$–$C_{12}$cycloalkyl, $C_1$–$C_4$alkyl-substituted $C_5$–$C_{12}$cycloalkyl, phenyl, —OH— and/or $C_1$–$C_{10}$alkyl-substituted phenyl, $C_7$–$C_9$phenylalkyl, $C_7$–$C_9$phenylalkyl which is substituted on the phenyl radical by —OH and/or $C_1$–$C_{10}$alkyl; or a group of the formula (IV),

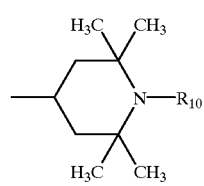

and the radicals $R_9$ and $R_{10}$ independently of one another are hydrogen, $C_1$–$C_8$alkyl or $C_1$–$C_{20}$acyl with 5 to 85% of the total sum of the radicals $R_9$ and $R_{10}$ independently of one another being hydrogen or $C_1$–$C_8$alkyl and the remaining radicals $R_9$ and $R_{10}$ being $C_1$–$C_{20}$acyl;

c) a product mixture of the formula

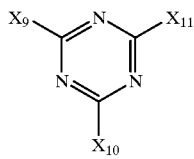

(V)

in which $X_9$, $X_{10}$ and $X_{11}$ independently of one another are a group of the formula (III) with 5 to 85% of the total sum of the radicals $R_9$ and $R_{10}$ independently of one another being hydrogen or $C_1$–$C_8$alkyl and the remaining radicals $R_9$ and $R_{10}$ being $C_1$–$C_{20}$acyl;

d)

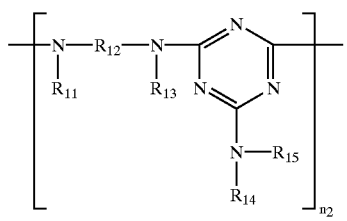

(VI)

in which $R_{11}$, $R_{13}$, $R_{14}$ and $R_{15}$ independently of one another are hydrogen, $C_1$–$C_{12}$alkyl, $C_5$–$C_{12}$cycloalkyl, $C_1$–$C_4$alkyl-substituted $C_5$–$C_{12}$cycloalkyl, phenyl, —OH— and/or $C_1$–$C_{10}$alkyl-substituted phenyl, $C_7$–$C_9$phenylalkyl, $C_7$–$C_9$phenylalkyl which is substituted on the phenyl radical by —OH and/or $C_1$–$C_{10}$alkyl; or a group of the formula (IV), $R_{12}$ is $C_2$–$C_{18}$alkylene, $C_5$–$C_7$cycloalkylene or $C_1$–$C_4$alkylenedi($C_5$–$C_7$cycloalkylene), or the radicals $R_{11}$, $R_{12}$ and $R_{13}$, together with the nitrogen atoms to which they are attached, form a 5- to 10-membered heterocyclic ring, or $R_{14}$ and $R_{15}$, together with the nitrogen atom to which they are attached, form a 5- to 10-membered heterocyclic ring, $n_2$ is a number from 2 to 50, and at least one of the radicals $R_{11}$, $R_{13}$, $R_{14}$ and $R_{15}$ is a group of the formula (IV) with 5 to 85% of the radicals $R_{10}$ independently of one another being hydrogen or $C_1$–$C_8$alkyl and the remaining radicals $R_{10}$ being $C_1$–$C_{20}$acyl;

e)

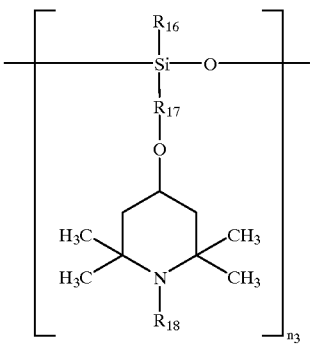

(VII)

in which $R_{16}$ is $C_1$–$C_{10}$alkyl, $C_5$–$C_{12}$cycloalkyl, $C_1$–$C_4$alkyl-substituted $C_5$–$C_{12}$cycloalkyl, phenyl or $C_1$–$C_{10}$alkyl-substituted phenyl, $R_{17}$ is $C_3$–$C_{10}$alkylene, the radicals $R_{18}$ independently of one another are hydrogen, $C_1$–$C_8$alkyl or $C_1$–$C_{20}$acyl with 5 to 85% of the radicals $R_{18}$ independently of one another being hydrogen or $C_1$–$C_8$alkyl and the remaining radicals $R_{18}$ being $C_1$–$C_{20}$acyl, and $n_3$ is a number from 2 to 50;

f) a product obtainable by reacting a compound, obtained by reaction between a polyamine of the formula (VIIIa) and cyanuric chloride, with a compound of the formula (VIIIb) or a mixture of the compounds (VIIIb) and (VIIIb*) to give an intermediate $H_2N$—$(CH_2)_{n'_4}$—$NH$—$(CH_2)_{n''_4}$—$NH$—$(CH_2)_{n'''_4}$—$NH_2$ (VIIIa)

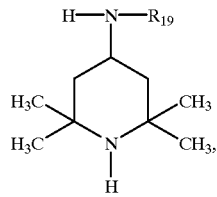

(VIIIb)

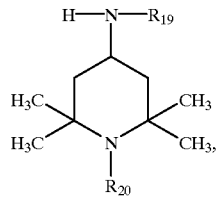

(VIIIb*)

in which $n'_4$, $n''_4$ and $n'''_4$ independently of one another are an integer from 2 to 12, $R_{19}$ is hydrogen, $C_1$–$C_{12}$alkyl, $C_5$–$C_{12}$cycloalkyl, phenyl or $C_7$–$C_9$phenylalkyl, and $R_{20}$ is $C_1$–$C_8$alkyl, with the proviso that in the mixture of the compounds (VIIIb) and (VIIIb*) at least 15% of the compound (VIIb) is present;

and subsequent acylation of the groups of the formula (A-1-a) being present in the intermediate

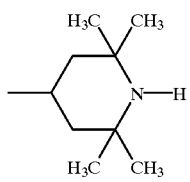
(A-1-a)

in a proportion to give a product which contains 15 to 95% of the groups of the formula (A-2)

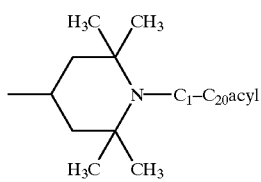
(A-2)

and 5 to 85% of the groups of the formula (A-1-a) and/or (A-1-b),

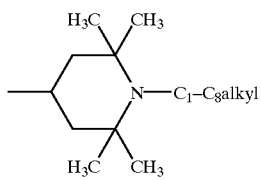
(A-1-b)

relative to the total sum of the groups (A-1-a), (A-1-b) and (A-2);

g)

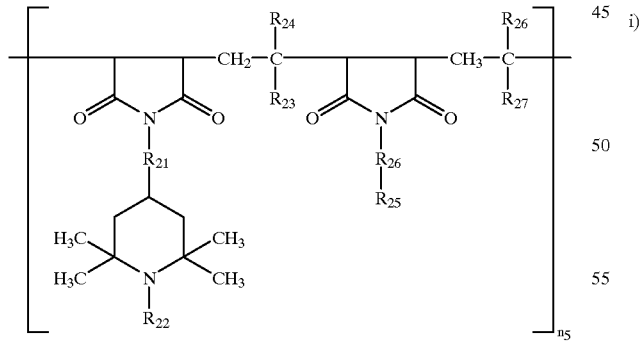
(IX)

in which
$R_{21}$ and $R_{26}$ independently of one another are a direct bond or a group —$N(Y_1)$—CO—$Y_2$—CO—$N(Y_3)$—, $Y_1$ and $Y_3$ independently of one another are hydrogen, $C_1$–$C_8$alkyl, $C_5$–$C_{12}$cycloalkyl, phenyl, $C_7$–$C_9$phenylalkyl or a group of the formula (IV), $Y_2$ is a direct bond or $C_1$–$C_4$alkylene, the radicals $R_{22}$ independently of one another are hydrogen, $C_1$–$C_8$alkyl or $C_1$–$C_{20}$acyl, $R_{23}$, $R_{24}$, $R_{27}$ and $R_{28}$ independently of one another are hydrogen, $C_1$–$C_{30}$alkyl, $C_5$–$C_{12}$cycloalkyl or phenyl, $R_{25}$ is hydrogen, $C_1$–$C_{30}$alkyl, $C_5$–$C_{12}$cycloalkyl, phenyl, $C_7$–$C_9$phenylalkyl or a group of the formula (IV) with 5 to 85% of the total sum of the radicals $R_{10}$ and $R_{22}$ independently of one another being hydrogen or $C_1$–$C_8$alkyl and the remaining radicals $R_{10}$ and $R_{22}$ being $C_1$–$C_{20}$acyl, and $n_5$ is a number from 2 to 50;

h) a product mixture of the formula

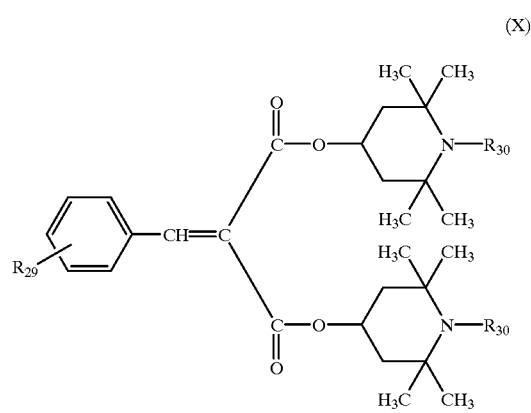
(X)

in which
$R_{29}$ is hydrogen, $C_1$–$C_{12}$alkyl or $C_1$–$C_{12}$alkoxy, and
the radicals $R_{30}$ independently of one another are hydrogen, $C_1$–$C_8$alkyl or $C_1$–$C_{20}$acyl with 5 to 85% of the total sum of the radicals $R_{30}$ independently of one another being hydrogen or $C_1$–$C_8$alkyl and the remaining radicals $R_{30}$ being $C_1$–$C_{20}$acyl;

i)

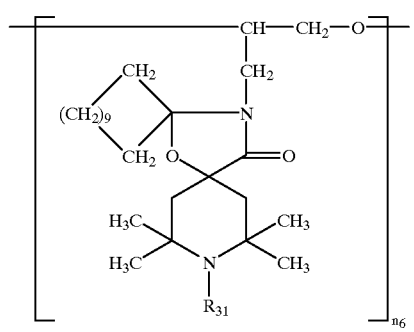
(XI)

in which
the radicals $R_{31}$ independently of one another are hydrogen, $C_1$–$C_8$alkyl or $C_1$–$C_{20}$acyl with 5 to 85% of the radicals $R_{31}$ independently of one another being hydrogen or $C_1$–$C_8$alkyl and the remaining radicals $R_{31}$ being $C_1$–$C_{20}$acyl, and $n_6$ is a number from 2 to 50;

j) a product mixture of the formula

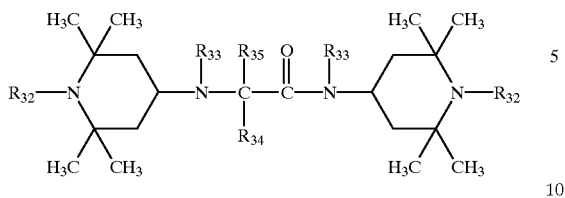

(XII)

in which
the radicals $R_{32}$ independently of one another are hydrogen, $C_1$–$C_8$alkyl or $C_1$–$C_{20}$acyl with 5 to 85% of the total sum of the radicals $R_{32}$ independently of one another being hydrogen or $C_1$–$C_8$alkyl and the remaining radicals $R_{32}$ being $C_1$–$C_{20}$acyl,
the radicals $R_{33}$ independently of one another are hydrogen, $C_1$–$C_{12}$alkyl or $C_1$–$C_{12}$acyl, and
$R_{34}$ and $R_{35}$ independently of one another are $C_1$–$C_{12}$alkyl;

k)

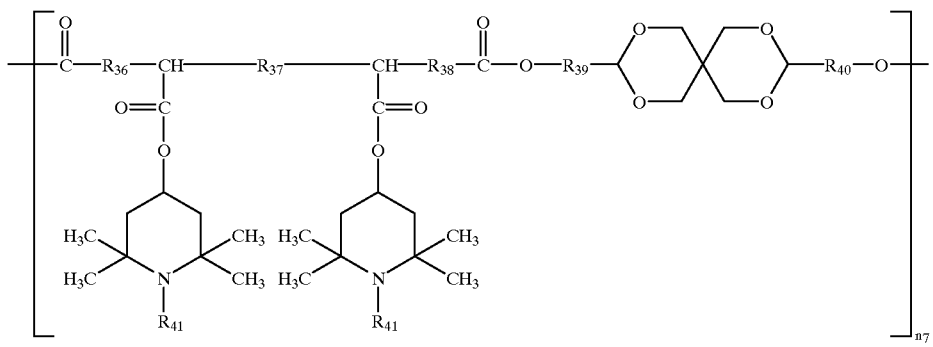

(XIII)

in which
$R_{36}$, $R_{37}$, $R_{38}$, $R_{39}$ and $R_{40}$ independently of one another are a direct bond or $C_1$–$C_{10}$alkylene, the radicals $R_{41}$ independently of one another are hydrogen, $C_1$–$C$ alkyl or $C_1$–$C_{20}$acyl with 5 to 85% of the radicals $R_{41}$ independently of one another being hydrogen or $C_1$–$C_8$alkyl and the remaining radicals $R_{41}$ being $C_1$–$C_{20}$acyl, and
$n_7$ is a number from 1 to 50;

l) a product mixture of the formula

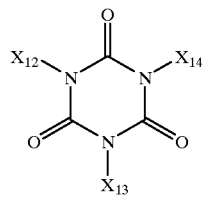

(XIV)

in which
$X_{12}$, $X_{13}$ and $X_{14}$ independently of one another are a group of the formula (XV),

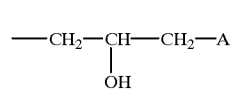

(XV)

in which A is a group of the formula (III) with 5 to 85% of the total sum of the radicals $R_9$ and $R_{10}$ independently of one another being hydrogen or $C_1$–$C_8$alkyl and the remaining radicals $R_9$ and $R_{10}$ being $C_1$–$C_{20}$acyl;

m) a product mixture of the formula

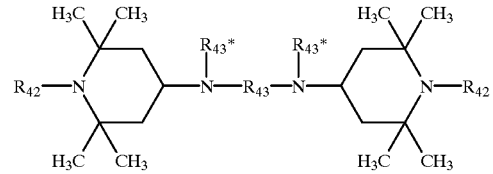

(XVI)

in which
the radicals $R_{42}$ independently of one another are hydrogen, $C_1$–$C_8$alkyl or $C_1$–$C_{20}$acyl with 5 to 85% of the total sum of the radicals $R_{42}$ independently of one another being hydrogen or $C_1$–$C_8$alkyl and the remaining radicals $R_{42}$ being $C_1$–$C_{20}$acyl,
the radicals $R_{43}$ independently of one another are $C_1$–$C_{20}$acyl, ($C_1$–$C_8$alkoxy)carbonyl, ($C_5$–$C_{12}$cycloalkoxy)carbonyl, ($C_1$–$C_8$alkyl)aminocarbonyl, ($C_5$–$C_{12}$cycloalkyl)aminocarbonyl, ($C_7$–$C_9$phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$, and $R_{43}$ is $C_2-C_{22}$alkylene, $C_5-C_7$cycloalkylene, $C_1-C_4$alkylenedi($C_5-C_7$cycloalkylene), phenylene or phenylenedi($C_1-C_4$alkylene);

n) a product mixture of the formula (XVII)

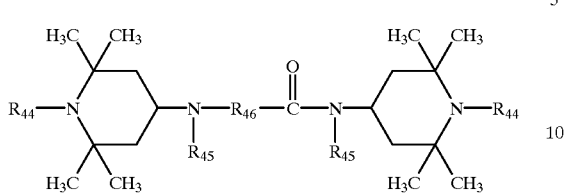

in which the radicals $R_{44}$ independently of one another are hydrogen, $C_1-C_8$ alkyl or $C_1-C_{20}$acyl with 5 to 85% of the total sum of the radicals $R_{44}$ independently of one another being hydrogen or $C_1-C_8$alkyl and the remaining radicals $R_{44}$ being $C_1-C_{20}$acyl, the radicals $R_{45}$ independently of one another are hydrogen, $C_1-C_{12}$alkyl or $C_1-C_{12}$acyl, and $R_{46}$ is $C_1-C_{10}$alkylene;

o) a product mixture of the formula (XVIII)

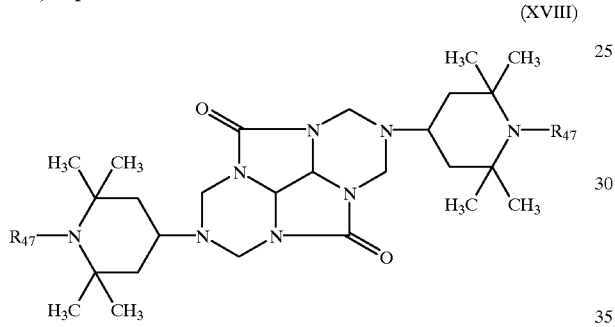

in which the radicals $R_{47}$ independently of one another are hydrogen, $C_1-C_8$alkyl or $C_1-C_{20}$acyl with 5 to 85% of the total sum of the radicals $R_{47}$ independently of one another being hydrogen or $C_1-C_8$alkyl and the remaining radicals $R_{47}$ being $C_1-C_{20}$acyl; or p)

(XIX)

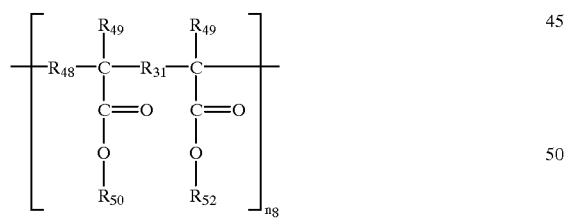

in which $R_{48}$ and $R_{51}$ independently of one another are $C_1-C_{10}$alkylene, the radicals $R_{49}$ independently of one another are hydrogen or $C_1-C_{10}$alkyl, $R_{50}$ is $C_1-C_{10}$alkyl, $R_{52}$ is $C_1-C_{10}$alkyl or a group of the formula (IV), and $n_8$ is a number from 3 to 50, with the proviso that at least 50% of the radicals $R_{52}$ are a group of the formula (IV) with 5 to 85% of the radicals $R_{10}$ independently of one another being hydrogen or $C_1-C_8$alkyl and the remaining radicals $R_{10}$ being $C_1-C_{20}$acyl.

3. A product according to claim 2 wherein $n_1$ is 2 or 4, if $n_1$ is 2, $R_2$ is $C_2-C_{10}$alkylene or bis{$C_1-C_{15}$alkyl}oxycarbonyl, and if $n_1$ is 4, $R_2$ is 1,2,3,4-butanetetrayl;

$R_3$ and $R_7$ independently of one another are hydrogen, $C_1-C_4$alkyl or $C_1-C_{20}$acyl, $R_4$, $R_5$ and $R_6$ independently of one another are $C_2-C_6$alkylene, and $R_8$ is hydrogen, $C_1-C_6$alkyl, $C_5-C_8$cycloalkyl, methyl-substituted $C_5-C_8$cycloalkyl, phenyl, $C_7-C_9$phenylalkyl or a group of the formula (IV);

$R_{11}$, $R_{13}$, $R_{14}$ and $R_{15}$ independently of one another are hydrogen, $C_1-C_8$alkyl, $C_5-C_8$cycloalkyl, methyl-substituted $C_5-C_8$cycloalkyl, phenyl, $C_7-C_9$phenylalkyl or a group of the formula (IV), or the radicals $R_{14}$ and $R_{15}$, together with the nitrogen atom to which they are attached, form a 6-membered heterocyclic ring, $R_{12}$ is $C_2-C_{10}$alkylene, and $n_2$ is a number from 2 to 25;

$R_{16}$ is $C_1-C_4$alkyl, $C_5-C_8$cycloalkyl or phenyl, $R_{17}$ is $C_3-C_6$alkylene, and $n_3$ is a number from 2 to 25;

$n'_4$, $n''_4$ and $n'''_4$ independently of one another are an integer from 2 to 4, and $R_{19}$ is $C_1-C_4$alkyl;

$R_{21}$ and $R_{26}$ independently of one another are a direct bond or a group $-N(Y_1)-CO-Y_2-CO-N(Y_3)-$, $Y_1$ and $Y_3$ independently of one another are hydrogen or $C_1-C_4$alkyl, $Y_2$ is a direct bond, $R_{23}$ and $R_{27}$ are $C_1-C_{25}$alkyl or phenyl, $R_{24}$ and $R_{28}$ are hydrogen or $C_1-C_4$alkyl, $R_{25}$ is $C_1-C_{25}$alkyl or a group of the formula (IV), and $n_5$ is a number from 2 to 25;

$R_{29}$ is hydrogen, $C_1-C_4$alkyl or $C_1-C_4$alkoxy;

$n_6$ is a number from 2 to 25;

the radicals $R_{33}$ independently of one another are hydrogen or $C_1-C_4$alkyl, and the radicals $R_{34}$ and $R_{35}$ independently of one another are $C_1-C_4$alkyl;

$R_{36}$, $R_{38}$, $R_{39}$ and $R_{40}$ independently of one another are $C_1-C_4$alkylene, $R_{37}$ is a direct bond, and $n_7$ is a number from 1 to 25;

$R_{43}$ is $C_2-C_6$alkylene, cyclohexylene or phenylene;

the radicals $R_{45}$ independently of one another are hydrogen or $C_1-C_4$alkyl, and $R_{46}$ is $C_2-C_6$alkylene; and $R_{48}$ and $R_{51}$ independently of one another are $C_1-C_6$alkylene, the radicals $R_{49}$ independently of one another are hydrogen or $C_1-C_4$alkyl, $R_{50}$ is $C_1-C_4$alkyl, $R_{52}$ is $C_1-C_4$alkyl or a group of the formula (IV), and $n_8$ is a number from 3 to 25.

4. A product according to claim 1 corresponding a) to a product mixture of the formula (I-a)

wherein 5 to 85% of the total sum of the radicals $R_1$ are hydrogen or methyl and the remaining radicals $R_1$ are $C_1-C_{10}$acyl;

to a product mixture of the formula

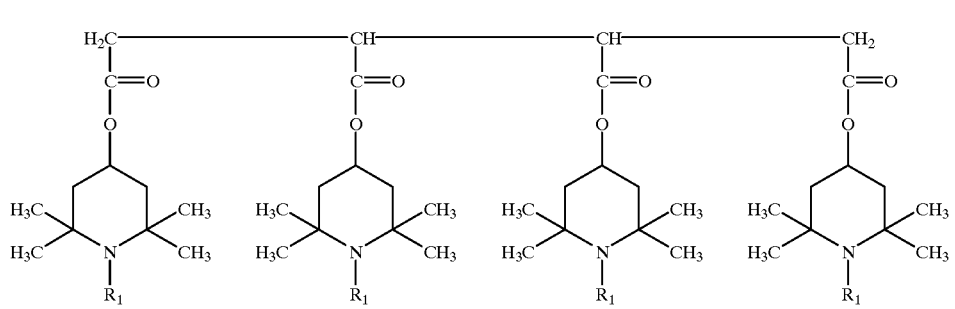

wherein 5 to 85% of the total sum of the radicals $R_1$ are hydrogen or methyl and the remaining radicals $R_1$ are $C_1$–$C_{10}$acyl; or to a product mixture of the formula

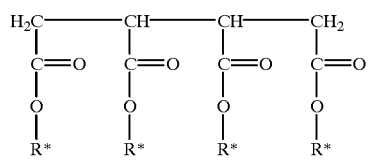

wherein two of the radicals R* are —COO—$C_{13}H_{27}$, and two of the radicals R* are a group

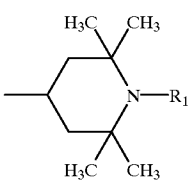

with 5 to 85% of the total sum of the radicals $R_1$ being hydrogen or methyl and the remaining radicals $R_1$ being $C_1$–$C_{10}$acyl;

b) to a product mixture of the formula (II-a)

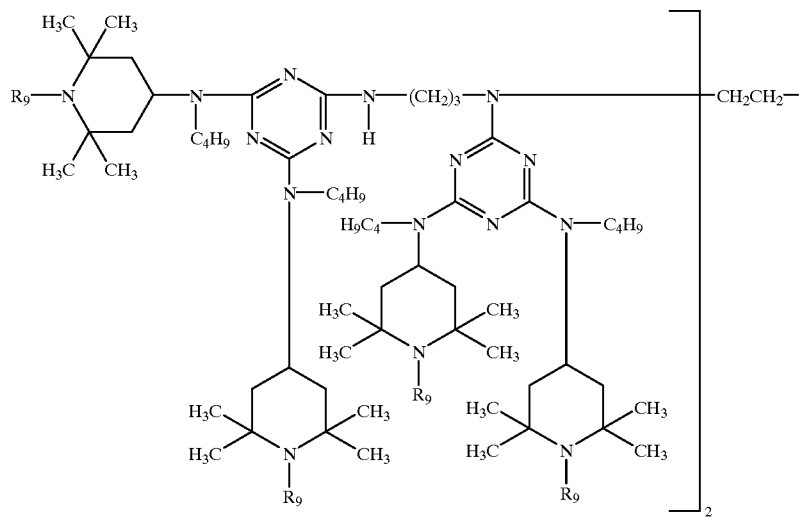

wherein 5 to 85% of the total sum of the radicals $R_9$ are hydrogen or methyl and the remaining radicals $R_9$ are $C_1$–$C_{10}$acyl;
c) to a product mixture of the formula (V-a)
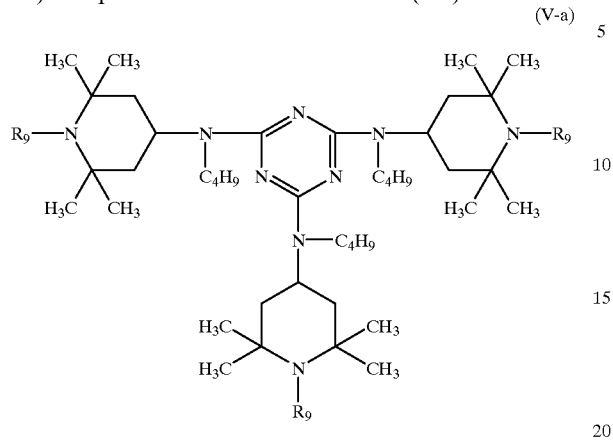
(V-a)
wherein 5 to 85% of the total sum of the radicals $R_9$ are hydrogen or methyl and the remaining radicals $R_9$ are $C_1$–$C_{10}$acyl;
d) to the formula (VI-a), (VI-b), (VI-c), (VI-d) or (VI-e)
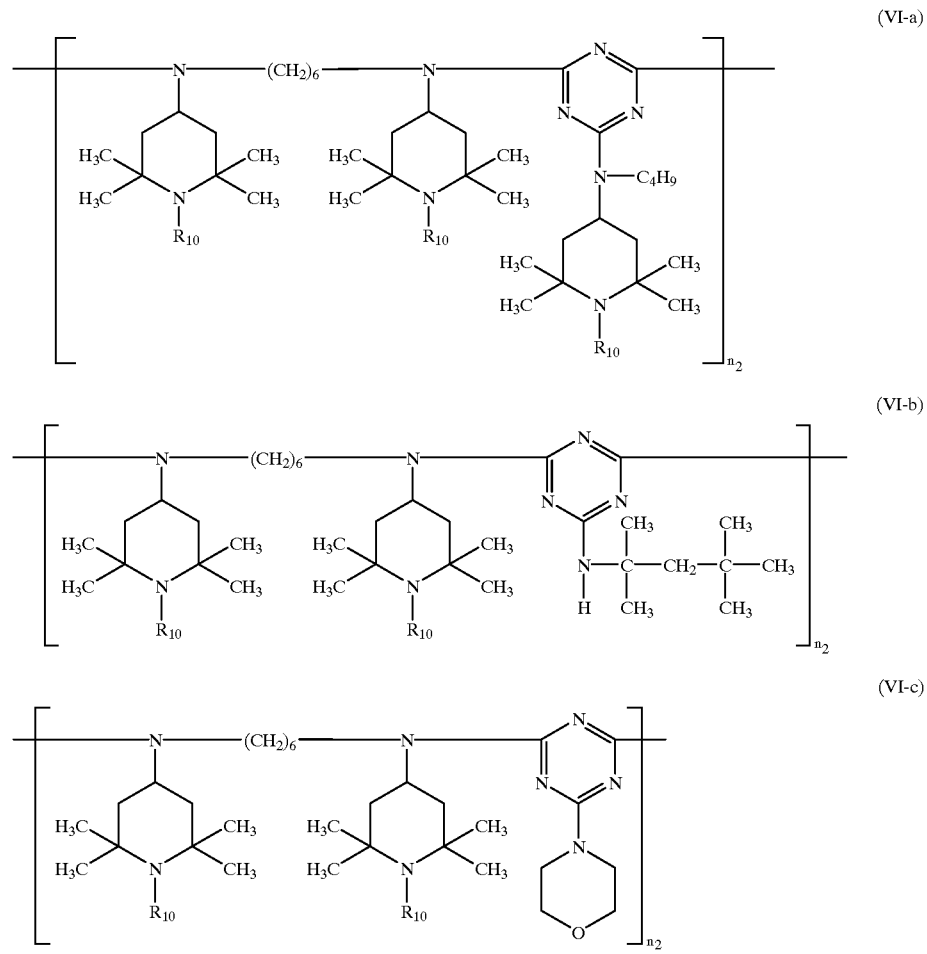

-continued

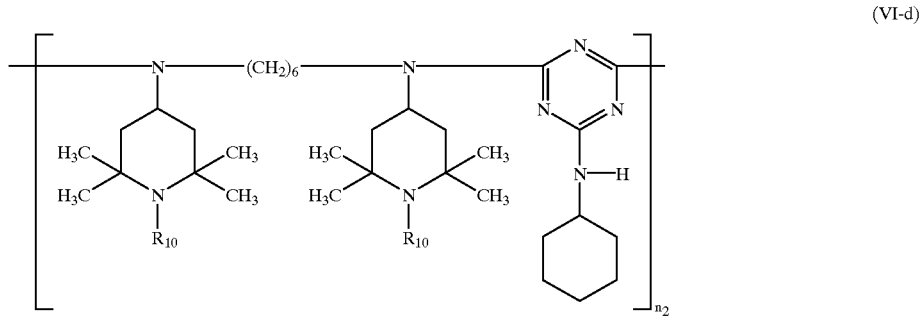
(VI-d)

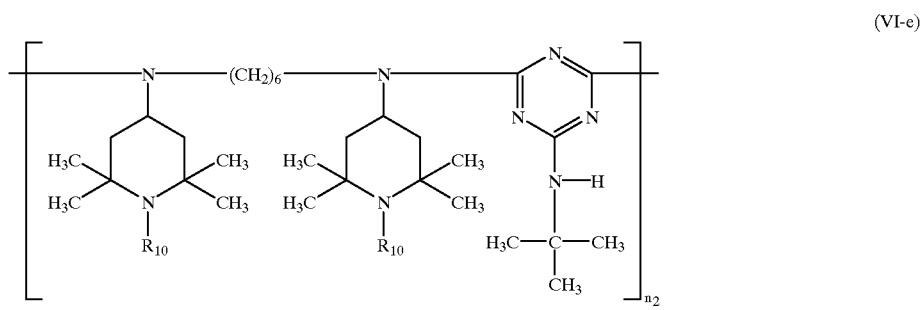
(VI-e)

wherein 5 to 85% of the radicals $R_{10}$ independently of one another are hydrogen or methyl and the remaining radicals $R_{10}$ are $C_1$–$C_{10}$acyl;

e) to the formula (VII-a)

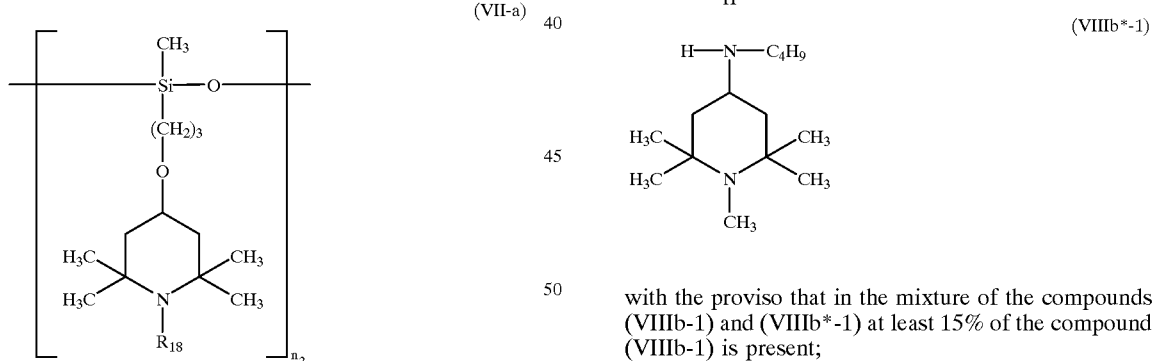
(VII-a)

wherein 5 to 85% of the radicals $R_{18}$ independently of one another are hydrogen or methyl and the remaining radicals $R_{18}$ are $C_1$–$C_{10}$acyl;

f) to a product obtainable by reacting a compound, obtained by reaction between a polyamine of the formula (VIIIa-1) and cyanuric chloride, with a compound of the formula (VIIIb-1) or a mixture of the compounds (VIIIb-1) and (VIIIb*-1) to give an intermediate $H_2N$—$(CH_2)_3$—$NH$—$(CH_2)_2$—$NH$—$(CH_2)_3$—$NH_2$  (VIIIa-1)

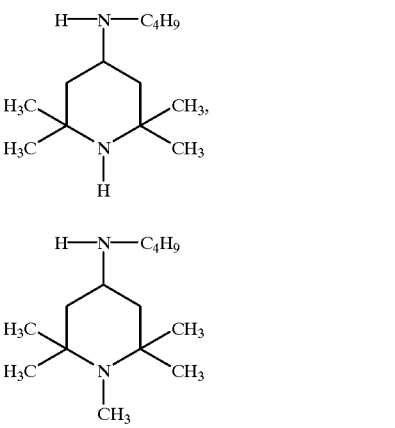
(VIIIb-1)

(VIIIb*-1)

with the proviso that in the mixture of the compounds (VIIIb-1) and (VIIIb*-1) at least 15% of the compound (VIIIb-1) is present;

and subsequent acylation of the groups of the formula (A-1-a) being present in the intermediate

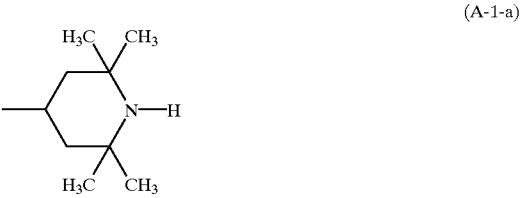
(A-1-a)

in a proportion to give a product which contains 15 to 95% of the groups of the formula (A-2-1)

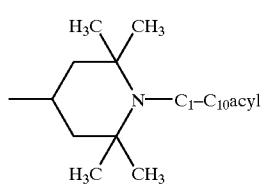
(A-2-1)
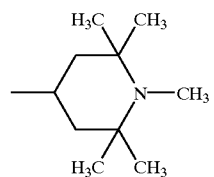
(A-1-b-1)
and 5 to 85% of the groups of the formula (A-1-a) and/or (A-1-b-1),
relative to the total sum of the groups (A-1-a), (A-1-b-1) and (A-2-1);
g) to the formula (IX-a), (IX-b) or (IX-c)
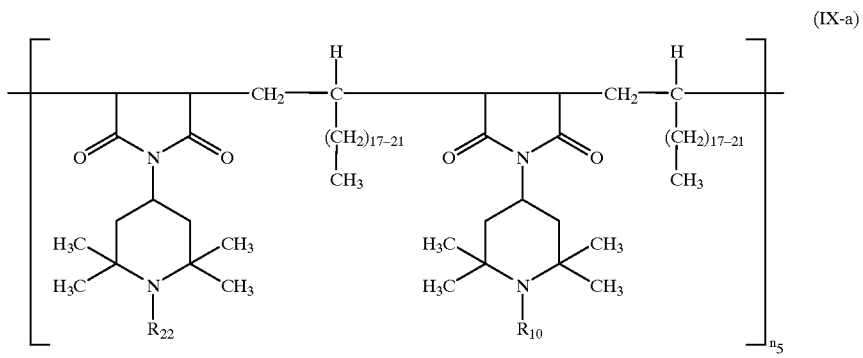
(IX-a)
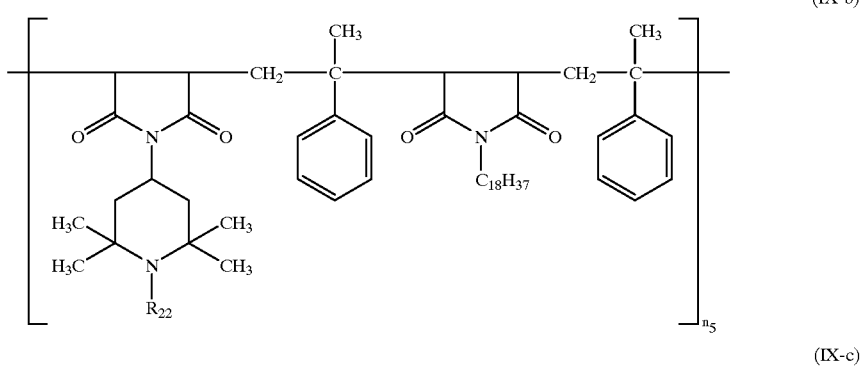
(IX-b)
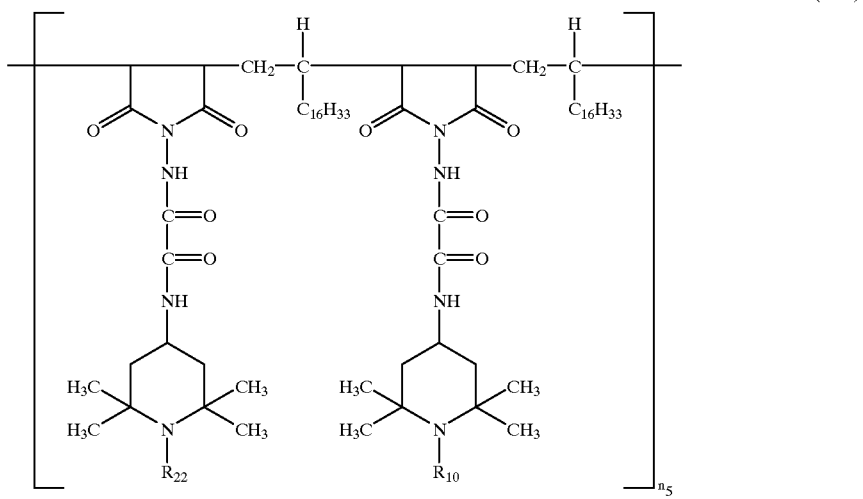
(IX-c)

wherein 5 to 85% of the radicals $R_{10}$ and $R_{22}$ independently of one another are hydrogen or methyl and the remaining radicals $R_{10}$ and $R_{22}$ are $C_1$–$C_{10}$acyl;

h) to a product mixture of the formula (X-a)

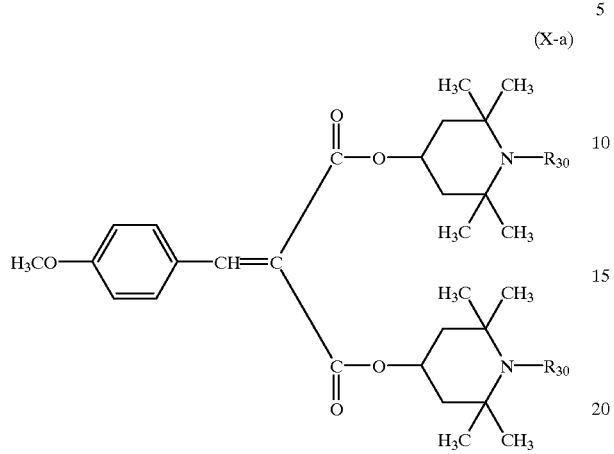

(X-a)

wherein 5 to 85% of the total sum of the radicals $R_{30}$ are hydrogen or methyl and the remaining radicals $R_{30}$ are $C_1$–$C_{10}$acyl;

i) to the formula (XI) wherein 5 to 85% of the radicals $R_{31}$ independently of one another are hydrogen or methyl and the remaining radicals $R_{31}$ are $C_1$–$C_{10}$acyl;

j) to a product mixture of the formula (XII-a)

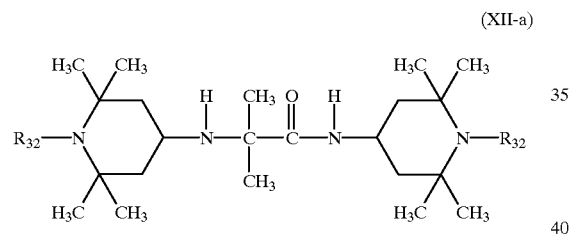

(XII-a)

wherein 5 to 85% of the total sum of the radicals $R_{32}$ are hydrogen or methyl and the remaining radicals $R_{32}$ are $C_1$–$C_{10}$acyl;

k) to the formula (XIII-a)

wherein 5 to 85% of the radicals $R_{41}$ independently of one another are hydrogen or methyl and the remaining radicals $R_{41}$ are $C_1$–$C_{10}$acyl;

l) to a product mixture of the formula (XIV-a)

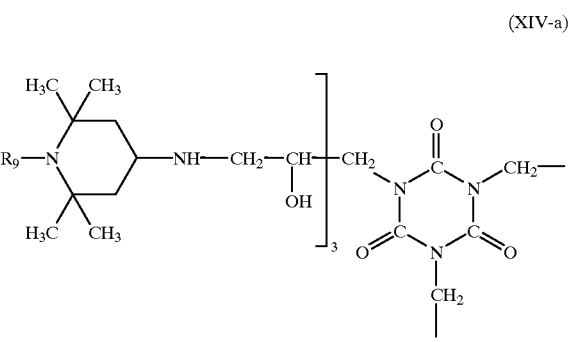

(XIV-a)

wherein 5 to 85% of the total sum of the radicals $R_9$ are hydrogen or methyl and the remaining radicals $R_9$ are $C_1$–$C_{10}$acyl;

m) to a product mixture of the formula (XVI-a)

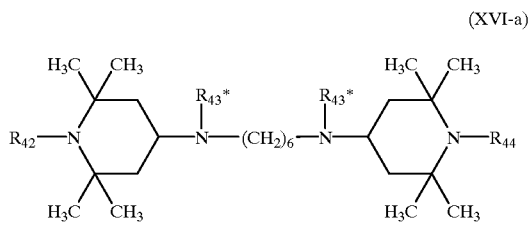

(XVI-a)

wherein 5 to 85% of the total sum of the radicals $R_{42}$ are hydrogen or methyl and the remaining radicals $R_{42}$ are $C_1$–$C_{10}$acyl; and the radicals $R_{43}*$ are $C_1$–$C_{10}$acyl;

(XIII-a)

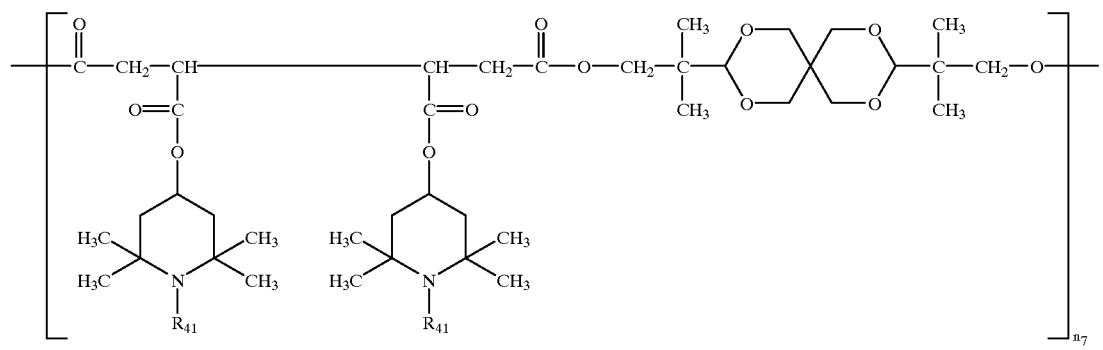

n) to a product mixture of the formula (XVII-a)

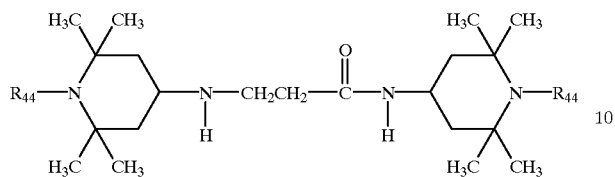

(XVII-a)

wherein 5 to 85% of the total sum of the radicals $R_{44}$ are hydrogen or methyl and the remaining radicals $R_{44}$ are $C_1$–$C_{10}$acyl;

o) to a product mixture of the formula (XVIII) wherein 5 to 85% of the total sum of the radicals $R_{47}$ are hydrogen or methyl and the remaining radicals $R_{47}$ are $C_1$–$C_{10}$acyl; or p) to the formula (XIX-a)

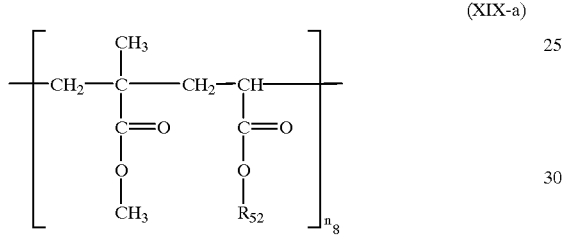

(XIX-a)

wherein the radicals $R_{52}$ independently of one another are ethyl or a group of the formula (IV),
with the provisos that (1) at least 50% of the radicals $R_{52}$ are a group of the formula (IV) with $R_{10}$ being hydrogen, methyl or $C_1$–$C_{10}$acyl, and the remaining radicals $R_{52}$ are ethyl and (2) 5 to 85% of the radicals $R_{10}$ independently of one another are hydrogen or methyl and the remaining radicals $R_{10}$ are $C_1$–$C_{10}$acyl.

5. A product according to claim 1, containing 20 to 70% of a group (A-1-a) and/or (A-1-b), and 30 to 80% of a group (A-2).

6. A product according to claim 1, containing 40 to 60% of a group (A-1-a) and/or (A-1-b), and 40 to 60% of a group (A-2).

7. A product according to claim 4 corresponding
a) to a product mixture of the formula (I-a)
wherein 20 to 70% of the total sum of the radicals $R_1$ are hydrogen or methyl and the remaining radicals $R_1$ are $C_1$–$C_{10}$acyl;
to a product mixture of the formula (I-b)
wherein 20 to 70% of the total sum of the radicals $R_1$ are hydrogen or methyl and the remaining radicals $R_1$ are $C_1$–$C_{10}$acyl; or
to a product mixture of the formula (I-c)
wherein 20 to 70% of the total sum of the radicals $R_1$ are hydrogen or methyl and the remaining radicals $R_1$ are $C_1$–$C_{10}$acyl;
b) to a product mixture of the formula (II-a)
wherein 20 to 70% of the total sum of the radicals $R_9$ are hydrogen or methyl and the remaining radicals $R_9$ are $C_1$–$C_{10}$acyl;
c) to a product mixture of the formula (V-a)
wherein 20 to 70% of the total sum of the radicals $R_9$ are hydrogen or methyl and the remaining radicals $R_9$ are $C_1$–$C_{10}$acyl;

d) to the formula (VI-a), (VI-b), (VI-c), (VI-d) or (VI-e)
wherein 20 to 70% of the radicals $R_{10}$ independently of one another are hydrogen or methyl and the remaining radicals $R_{10}$ are $C_1$–$C_{10}$acyl;

e) to the formula (VII-a)
wherein 20 to 70% of the radicals $R_{18}$ independently of one another are hydrogen or methyl and the remaining radicals $R_{18}$ are $C_1$–$C_{10}$acyl;

f) to a product obtainable by reacting a compound, obtained by reaction between a polyamine of the formula (VIIIa-1) and cyanuric chloride, with a compound of the formula (VIIIb-1) or a mixture of the compounds (VIIIb-1) and (VIIIb*-1) to give an intermediate with the proviso that in the mixture of the compounds (VIIIb-1) and (VIIIb*-1) at least 30% of the compound (VIIIb-1) is present;
and subsequent acylation of the groups of the formula (A-1-a) being present in the intermediate
in a proportion to give a product which contains 30 to 80% of the groups of the formula (A-2-1)
and 20 to 70% of the groups of the formula (A-1-a) and/or (A-1-b-1), relative to the total sum of the groups (A-1-a), (A-1-b-1) and (A-2-1);

g) to the formula (IX-a), (IX-b) or (IX-c)
wherein 20 to 70% of the radicals $R_{10}$ and $R_{22}$ independently of one another are hydrogen or methyl and the remaining radicals $R_{10}$ and $R_{22}$ are $C_1$–$C_{10}$acyl;

h) to a product mixture of the formula (X-a)
wherein 20 to 70% of the total sum of the radicals $R_{30}$ are hydrogen or methyl and the remaining radicals $R_{30}$ are $C_1$–$C_{10}$acyl;

i) to the formula (XI) wherein 20 to 70% of the radicals $R_{31}$ independently of one another are hydrogen or methyl and the remaining radicals $R_{31}$ are $C_1$–$C_{10}$acyl;

j) to a product mixture of the formula (XII-a)
wherein 20 to 70% of the total sum of the radicals $R_{32}$ are hydrogen or methyl and the remaining radicals $R_{32}$ are $C_1$–$C_{10}$acyl;

k) to the formula (XIII-a)
wherein 20 to 70% of the radicals $R_{41}$ independently of one another are hydrogen or methyl and the remaining radicals $R_{41}$ are $C_1$–$C_{10}$acyl;

l) to a product mixture of the formula (XIV-a)
wherein 20 to 70% of the total sum of the radicals $R_9$ are hydrogen or methyl and the remaining radicals $R_9$ are $C_1$–$C_{10}$acyl;

m) to a product mixture of the formula (XVI-a)
wherein 20 to 70% of the total sum of the radicals $R_{42}$ are hydrogen or methyl and the remaining radicals $R_{42}$ are $C_1$–$C_{10}$acyl;

n) to a product mixture of the formula (XVII-a)
wherein 20 to 70% of the total sum of the radicals $R_{44}$ are hydrogen or methyl and the remaining radicals $R_{44}$ are $C_1$–$C_{10}$acyl;

o) to a product mixture of the formula (XVIII) wherein 20 to 70% of the total sum of the radicals $R_{47}$ are hydrogen or methyl and the remaining radicals $R_{47}$ are $C_1$–$C_{10}$acyl; or p) to the formula (XIX-a)
wherein 20 to 70% of the radicals $R_{10}$ independently of one another are hydrogen or methyl and the remaining radicals $R_{10}$ are $C_1$–$C_{10}$acyl.

8. A product according to claim 4 corresponding
a) to a product mixture of the formula (I-a)
    wherein 15 to 30% of the total sum of the radicals $R_1$ are hydrogen or methyl and the remaining radicals $R_1$ are $C_1$–$C_{10}$acyl;
b) to a product mixture of the formula (II-a)
    wherein 30 to 50% of the total sum of the radicals $R_9$ are hydrogen or methyl and the remaining radicals $R_9$ are $C_1$–$C_{10}$acyl;
d) to the formula (VI-a)
    wherein 15 to 85% of the radicals $R_{10}$ independently of one another are hydrogen or methyl and the remaining radicals $R_{10}$ are $C_1$–$C_{10}$acyl; or
    to the formula (VI-b) or (VI-c)
    wherein 15 to 60% of the radicals $R_{10}$ independently of one another are hydrogen or methyl and the remaining radicals $R_{10}$ are $C_1$–$C_{10}$acyl;
e) to the formula (VII-a)
    wherein 15 to 35% of the radicals $R_{18}$ independently of one another are hydrogen or methyl and the remaining radicals $R_{18}$ are $C_1$–$C_{10}$acyl;
f) to a product obtainable by reacting a compound, obtained by reaction between a polyamine of the formula (VIIIa-1) and cyanuric chloride, with a compound of the formula (VIIIb-1) or a mixture of the compounds (VIIIb-1) and (VIIIb*-1) to give an intermediate with the proviso that in the mixture of the compounds (VIIIb-1) and (VIIIb*-1) at least 50% of the compound (VIIIb-1) is present;
    and subsequent acylation of the groups of the formula (A-1-a) being present in the intermediate
    in a proportion to give a product which contains 50 to 70% of the groups of the formula (A-2-1)
    and 30 to 50% of the groups of the formula (A-1-a) and/or (A-1-b-1), relative to the total sum of the groups (A-1-a), (A-1-b-1) and (A-2-1);
k) to the formula (XIII-a)
    wherein 15 to 30% of the radicals $R_{41}$ independently of one another are hydrogen or methyl and the remaining radicals $R_{41}$ are $C_1$–$C_{10}$acyl; or
m) to a product mixture of the formula (XVI-a)
    wherein 30 to 50% of the total sum of the radicals $R_{42}$ are hydrogen or methyl and the remaining radicals $R_{42}$ are $C_1$–$C_{10}$acyl.

9. A product according to claim 4 wherein the meaning $C_1$–$C_{10}$acyl is acetyl.

10. A product according to claim 4, which corresponds to the formula (VI-a) wherein 40 to 60% of the radicals $R_{10}$ independently of one another are hydrogen or methyl.

11. A product according to claim 4, which corresponds to the formula (VI-a) wherein 40 to 60% of the radicals $R_{10}$ are hydrogen and the remaining radicals $R_{10}$ are acetyl.

* * * * *